US011193173B2

(12) United States Patent
Kim et al.

(10) Patent No.: US 11,193,173 B2
(45) Date of Patent: Dec. 7, 2021

(54) **NANO-VESICLES DERIVED FROM BACTERIA OF GENUS *PROPIONIBACTERIUM* AND USE THEREOF**

(71) Applicants: MD HEALTHCARE INC., Seoul (KR); POSTECH ACADEMY-INDUSTRY FOUNDATION, Gyeongsangbuk-do (KR)

(72) Inventors: Yoon-Keun Kim, Gyeonggi-do (KR); Changill Ban, Gyeongsangbuk-do (KR); Jinseong Jeon, Gwangju (KR)

(73) Assignee: MD HEALTHCARE INC.

( * ) Notice: Subject to any disclaimer, the term of this patent is extended or adjusted under 35 U.S.C. 154(b) by 128 days.

(21) Appl. No.: 16/315,683

(22) PCT Filed: Jun. 29, 2017

(86) PCT No.: PCT/KR2017/006889
§ 371 (c)(1),
(2) Date: Jan. 7, 2019

(87) PCT Pub. No.: WO2018/008895
PCT Pub. Date: Jan. 11, 2018

(65) Prior Publication Data
US 2019/0345561 A1   Nov. 14, 2019

(30) Foreign Application Priority Data

Jul. 8, 2016 (KR) .................. 10-2016-0087058
Jun. 28, 2017 (KR) .................. 10-2017-0081782

(51) Int. Cl.
*C12Q 1/6886* (2018.01)
*A23L 33/135* (2016.01)
*A61P 17/00* (2006.01)
*A61P 29/00* (2006.01)
*A61P 35/00* (2006.01)
*A61K 8/99* (2017.01)
*A61K 35/741* (2015.01)
*A61K 39/02* (2006.01)
*A61K 39/05* (2006.01)
*A61K 39/00* (2006.01)

(52) U.S. Cl.
CPC .......... *C12Q 1/6886* (2013.01); *A23L 33/135* (2016.08); *A61K 8/99* (2013.01); *A61K 35/741* (2013.01); *A61K 39/02* (2013.01); *A61K 39/05* (2013.01); *A61P 17/00* (2018.01); *A61P 29/00* (2018.01); *A61P 35/00* (2018.01); *A61K 2039/55555* (2013.01); *C12Q 2600/112* (2013.01); *C12Q 2600/118* (2013.01)

(58) Field of Classification Search
None
See application file for complete search history.

(56) References Cited

FOREIGN PATENT DOCUMENTS

| EP | 2484752 A2 | 8/2012 |
| JP | 2016-028033 A | 2/2016 |
| KR | 10-1459166 B1 | 9/2009 |
| WO | 2013050583 A1 | 4/2013 |

OTHER PUBLICATIONS

Butler-Wu, S.M. et al., Optimization of Periprosthetic Culture for Diagnosis of Propionibacterium acnes Prosthetic Joint Infection, J. Clin. Microbiol., vol. 49, pp. 2490-2495 (Year: 2011).*
Shinohara et al (Prostate 73:1007-1015, 2013).*
Choi et al (J. Investigative Derm., 138:1371-1379, 2018).*
Davidsson et al., "Frequency and typing of Propionibacterium acnes in prostate tissue obtained from men with and without prostate cancer," Infectious Agents and Cancer, 2016, vol. 11, No. 26, pp. 1-10.
Choi et al., "Decreased diversity of nasal microbiota and their secreted extracellular vesicles in patients with chronic rhinosinusitis based on a metagenomic analysis," Allergy, 2014, vol. 69, pp. 517-526.
Sfanos et al., "An evaluation of PCR primer sets used for detection of Propionibacterium acnes in prostate tissue samples," The Prostate, 2008, vol. 68, pp. 1492-1495.
Extended European Search Report for corresponding European Patent Application No. 17824451.3 dated Feb. 18, 2020 (pp. 4-13).
Notice of Rejection for corresponding Japanese Patent Application No. 2019-500448 dated Mar. 17, 2020 (pp. 5-10).

(Continued)

*Primary Examiner* — Brian Gangle
(74) *Attorney, Agent, or Firm* — Riverside Law LLP

(57) ABSTRACT

The present invention relates to vesicles derived from bacteria of the genus *Propionibacterium* and a use thereof. It was experimentally confirmed that the production of vesicles derived from bacteria of the genus *Propionibacterium* was increased in the body by a high-fat diet rather than a high-carbohydrate diet; the vesicles were significantly reduced in the blood of patients with cancers, such as breast cancer and liver cancer, inflammation diseases, such as asthma and atopic dermatitis, and metabolic diseases, such as diabetes and liver cirrhosis, compared with normal persons; and the vesicles inhibited the secretion of inflammatory mediators by pathogenic vesicles, inhibited the apoptosis of keratinocytes, and increased the expression of an androgen receptor in the body. The vesicles derived from bacteria of the genus *Propionibacterium* according to the present invention are expected to be advantageously used in a method for diagnosis or prediction of cancers, inflammatory diseases, endocrine diseases, or metabolic diseases, a pharmaceutical composition, a food, a cosmetic product, and the like.

4 Claims, 23 Drawing Sheets
Specification includes a Sequence Listing.

(56) References Cited

OTHER PUBLICATIONS

Lusta KA, Kozlovskiĭ IuE. Outer Membrane Nanovesicles of Gram-Negative Bacteria Aeromonas hydrophila and Aeromonas salmonicida. Mikrobiologiia. 2011;80(4):513-518. (cited in EESR for EP 17824451.3 dated Feb. 18, 2020).

Dorward DW, Garon CF. DNA Is Packaged within Membrane-Derived Vesicles of Gram-Negative but Not Gram-Positive Bacteria. Appl Environ Microbiol. 1990;56(6): 1960-1962. (cited in EESR for EP 17824451.3 dated Feb. 18, 2020).

Hong SW, Kim MR, Lee EY, et al. Extracellular vesicles derived from *Staphylococcus aureus* induce atopic dermatitis-like skin inflammation. Allergy. 2011;66(3):351-359. (cited in EESR for EP 17824451.3 dated Feb. 18, 2020).

Jeon J, Mok HJ, Choi Y, et al. Proteomic analysis of extracellular vesicles derived from Propionibacterium acnes. Proteomics Clin Appl. 2017;11(1-2). (cited in OA for JP 2019-500448 dated Mar. 17, 2020).

Office Action for corresponding European Patent Application No. 17824451.3 dated Aug. 20, 2021.

Butler-Wu SM, Burns EM, Pottinger PS, et al. Optimization of periprosthetic culture for diagnosis of Propionibacterium acnes prosthetic joint infection. J Clin Microbiol. 2011;49(7):2490-2495 (cited in OA for EP 17824451.3 dated Aug. 20, 2021).

\* cited by examiner

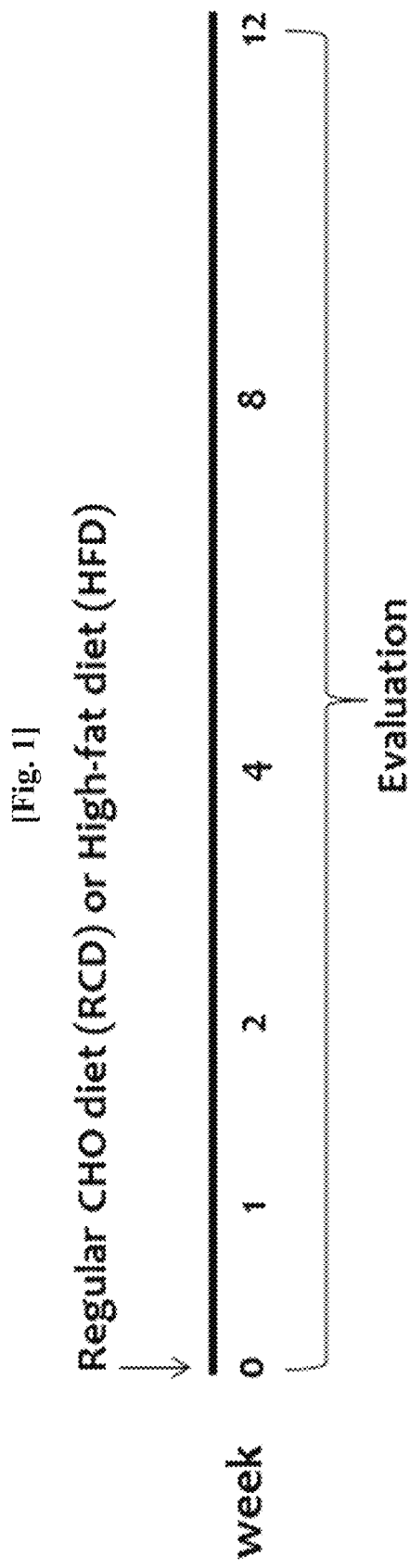

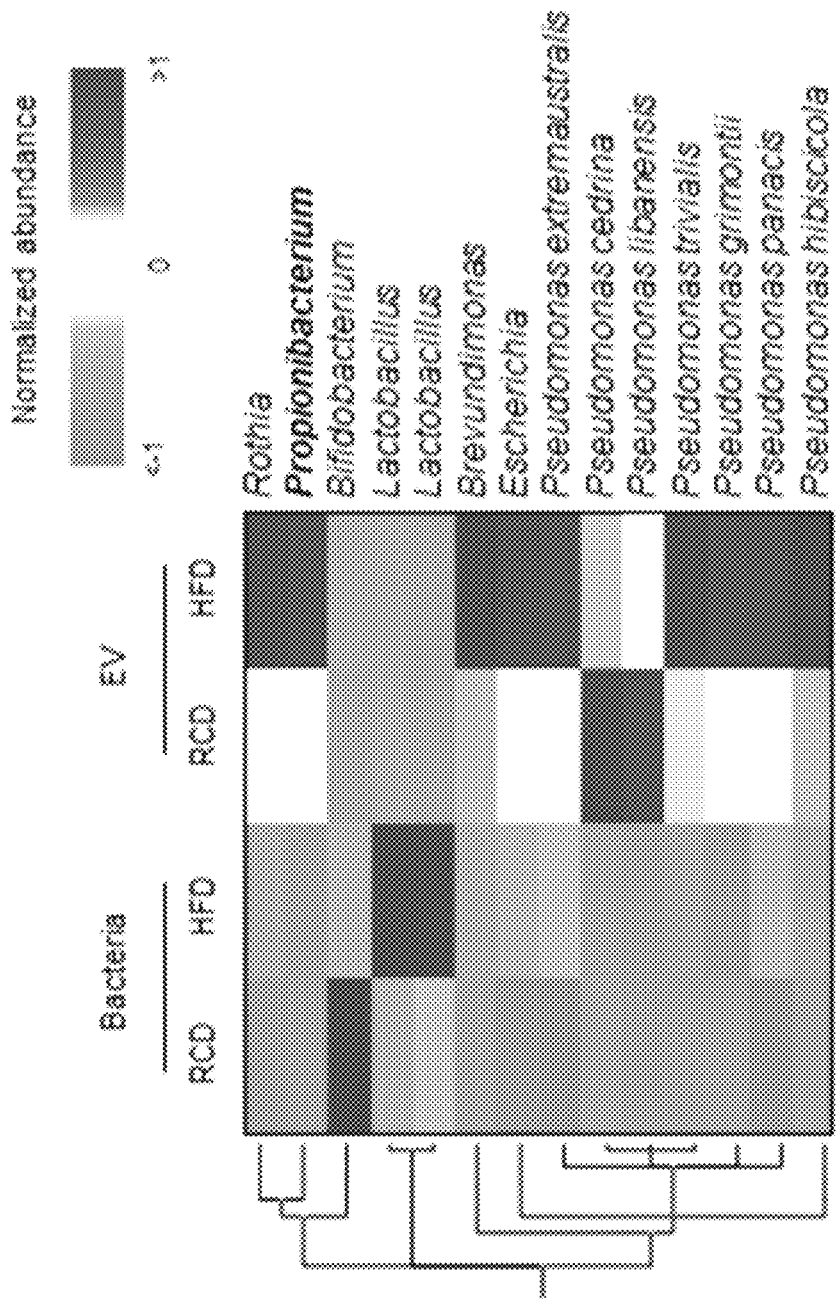
[Fig. 2]

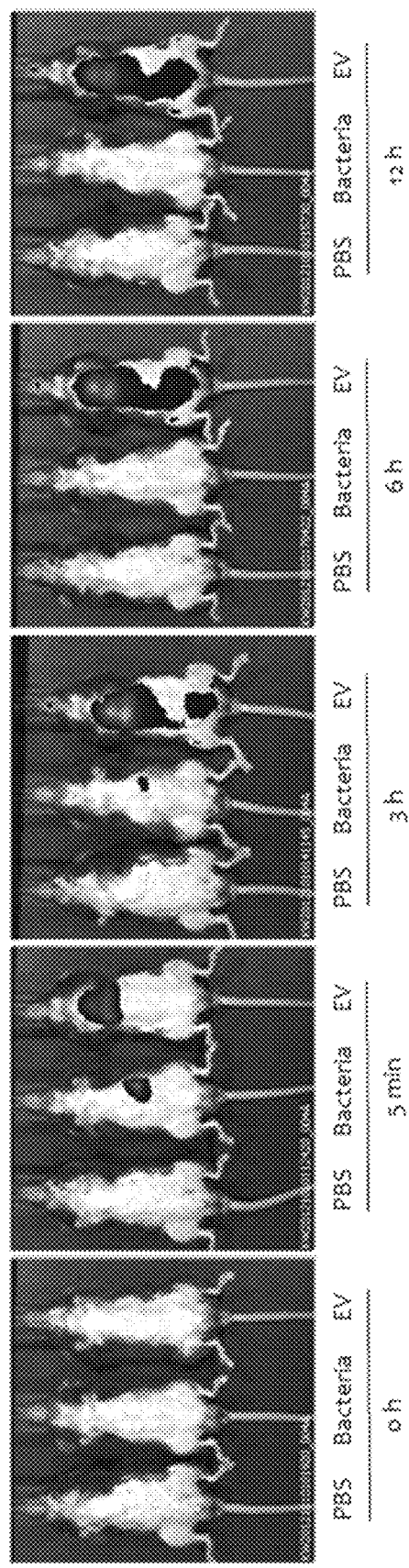
[Fig. 3A]

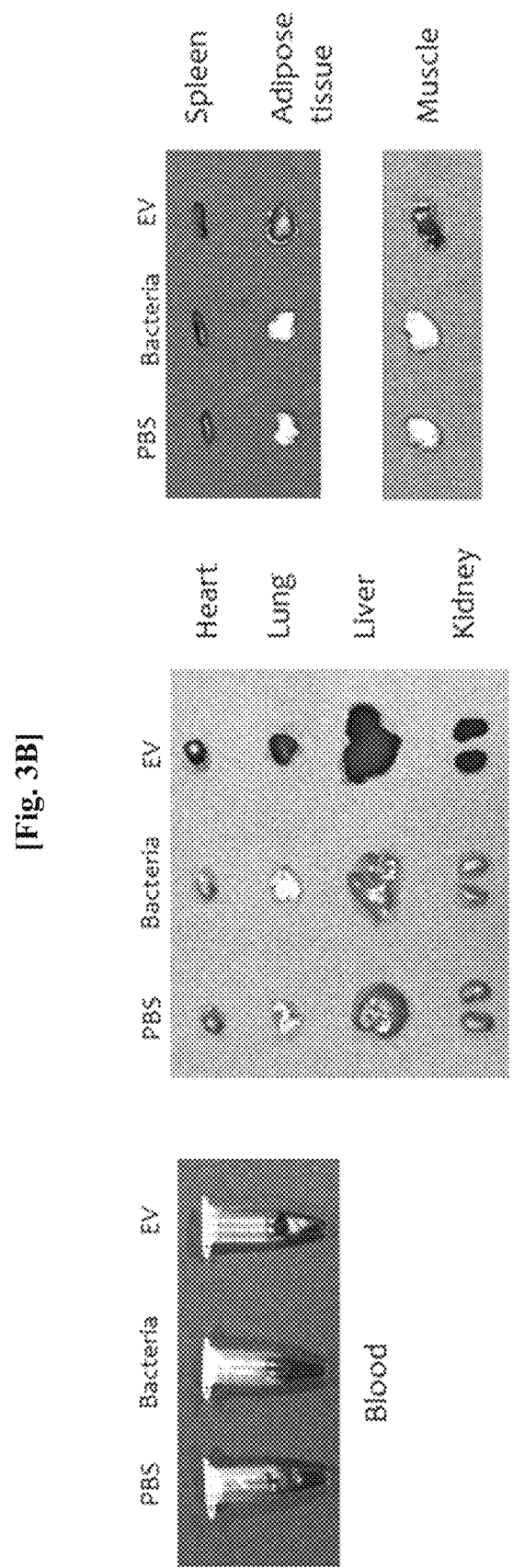

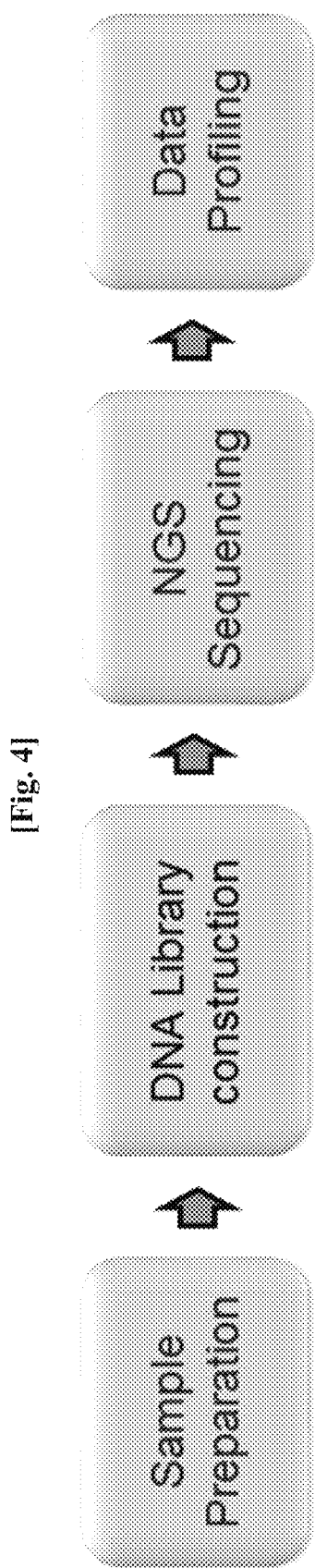
[Fig. 4]

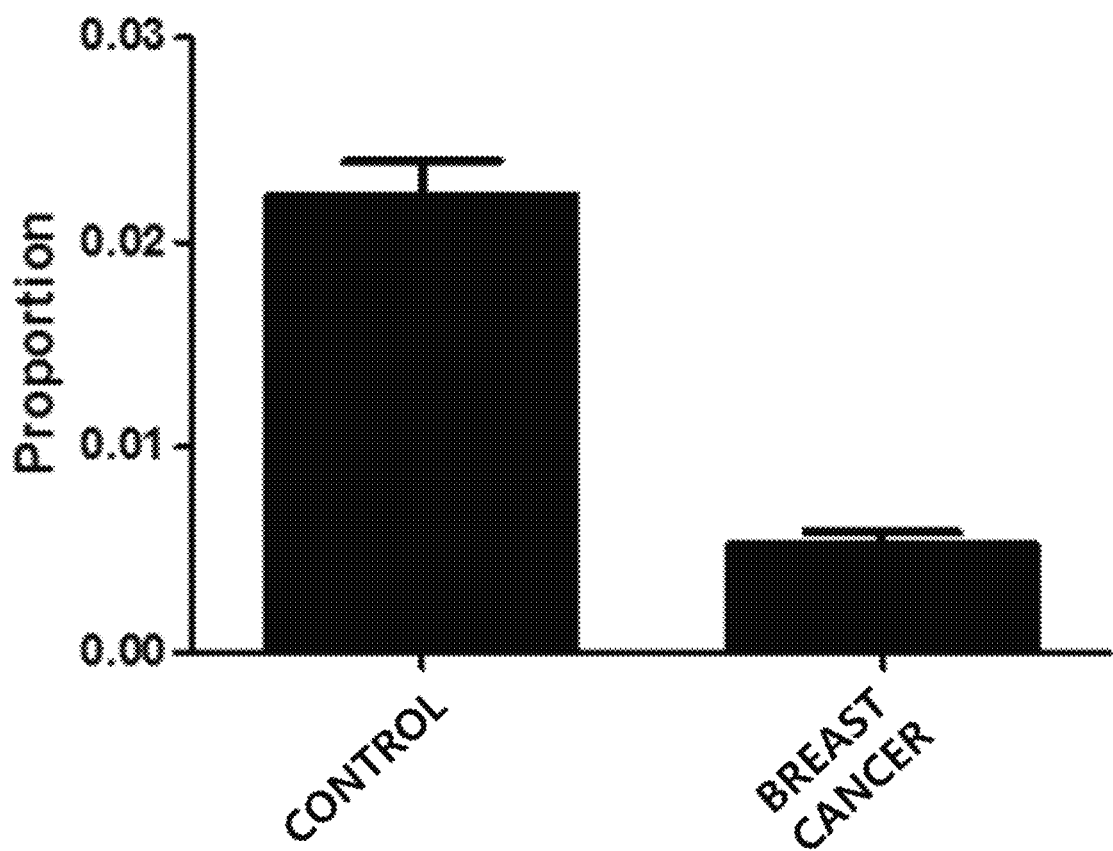
[Fig. 5A]

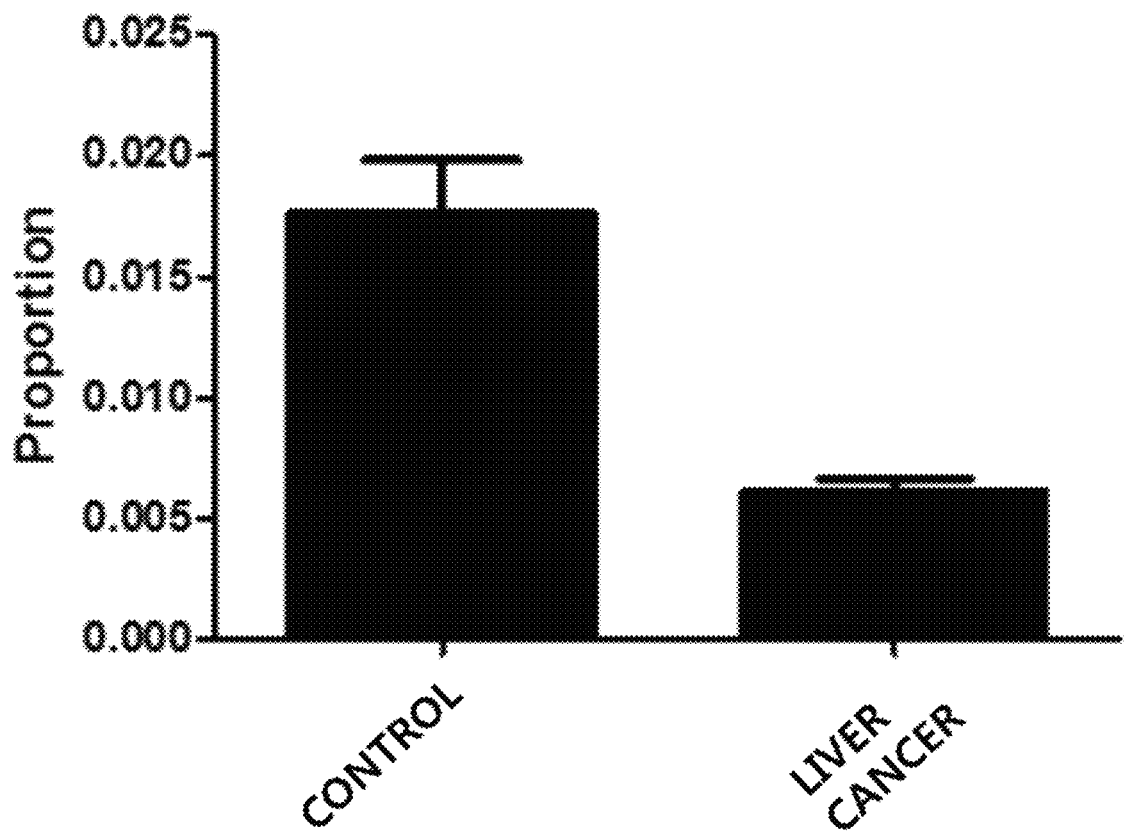
[Fig. 5B]

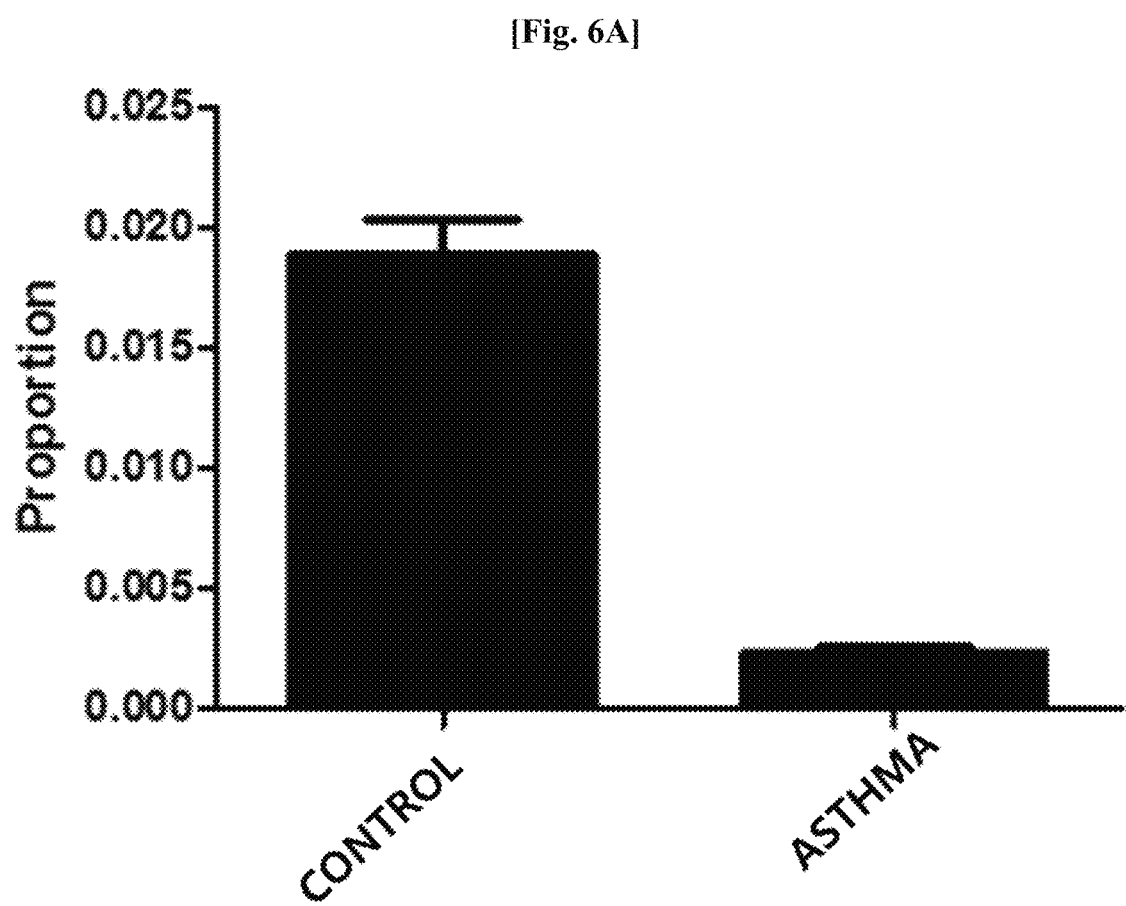
[Fig. 6A]

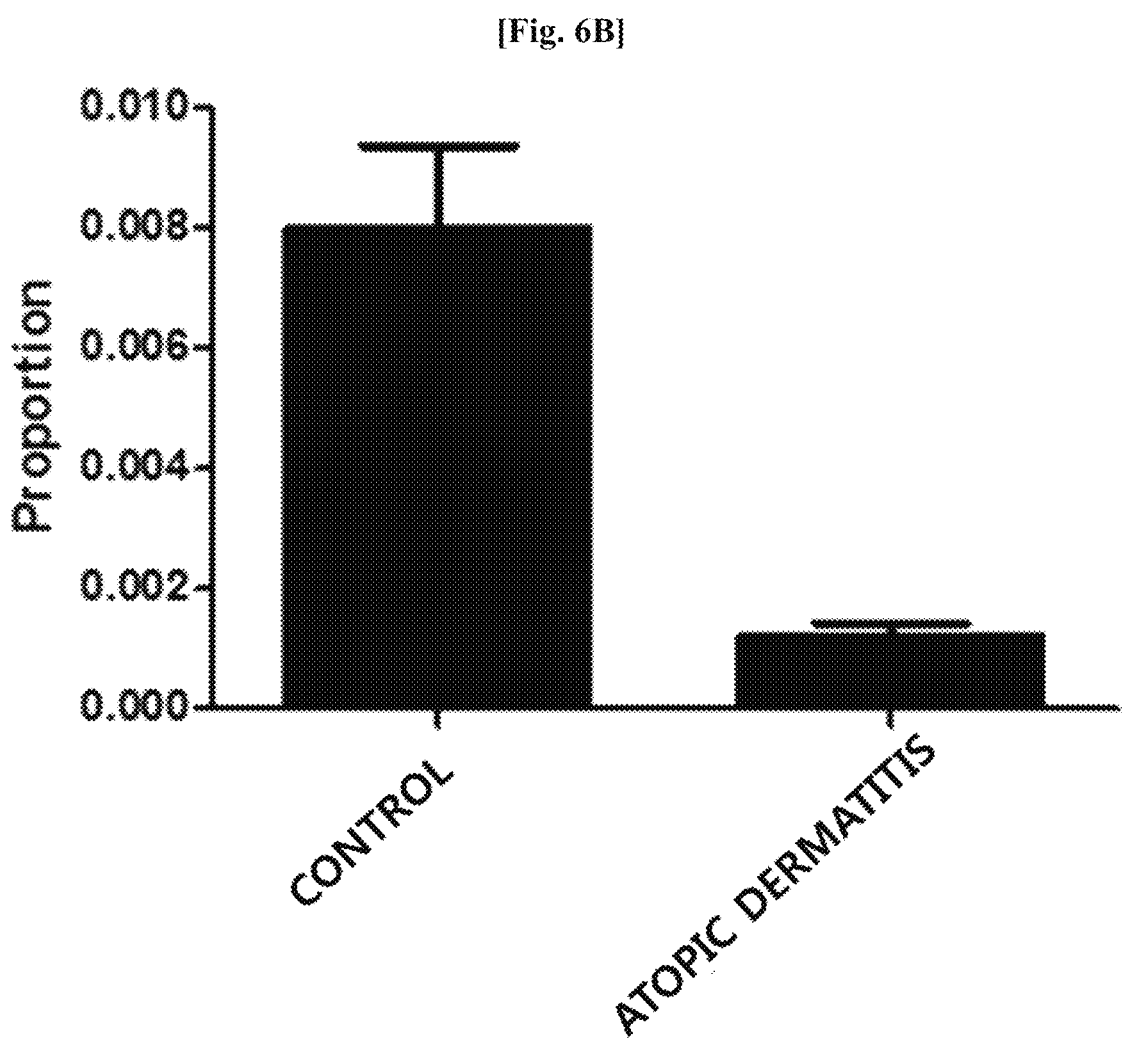
[Fig. 6B]

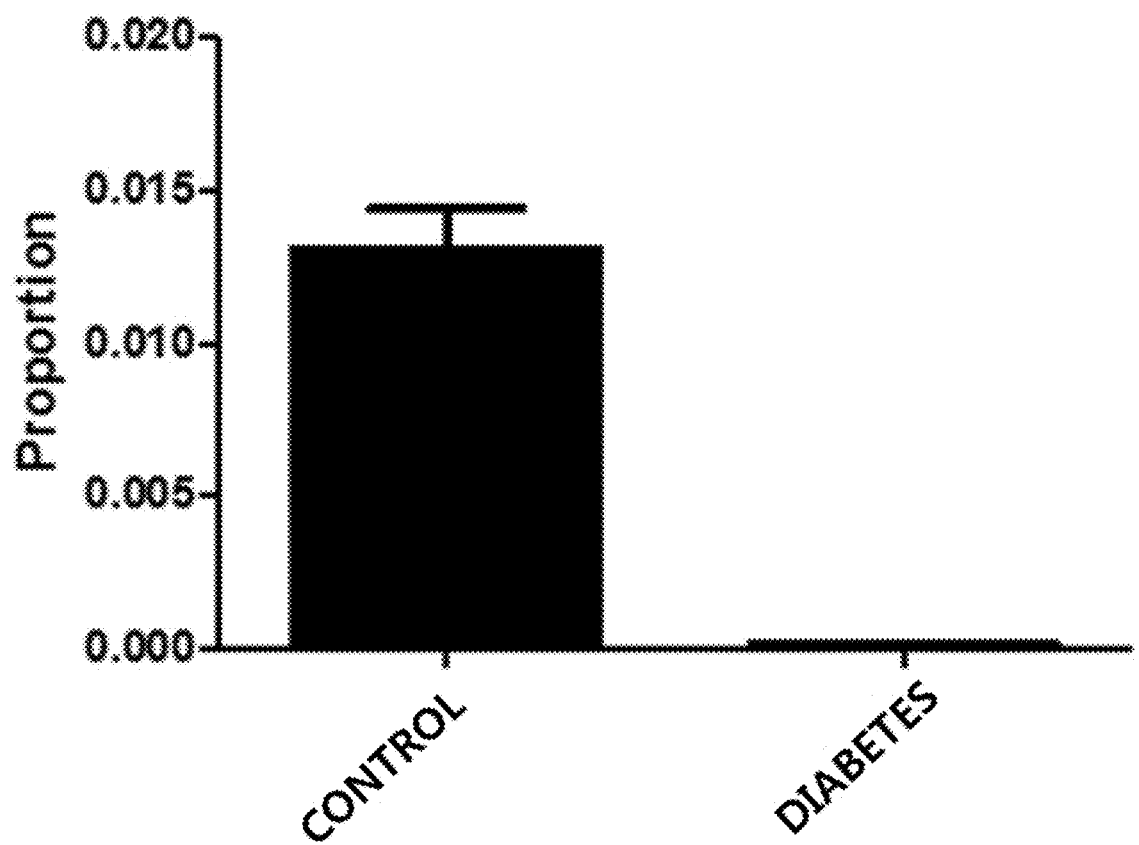
[Fig. 7A]

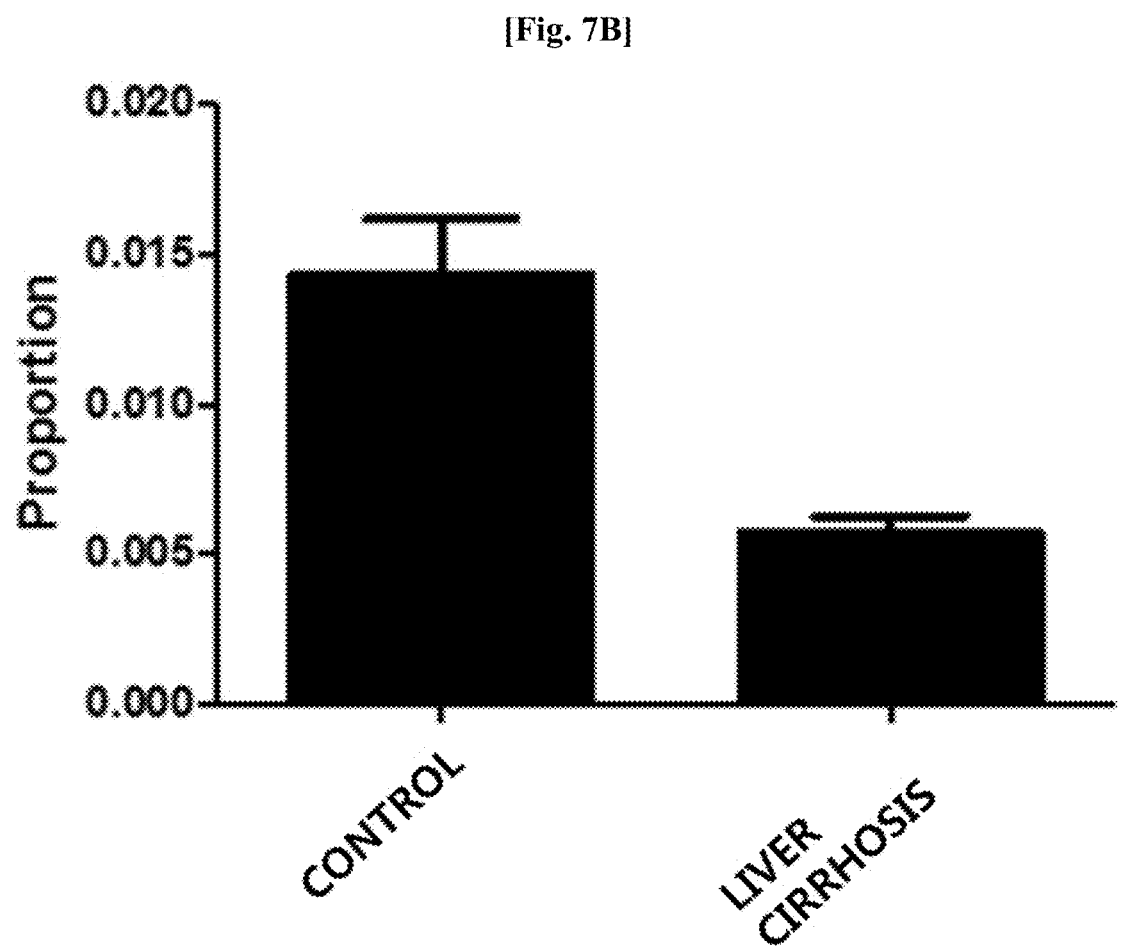
[Fig. 7B]

[Fig. 8A]
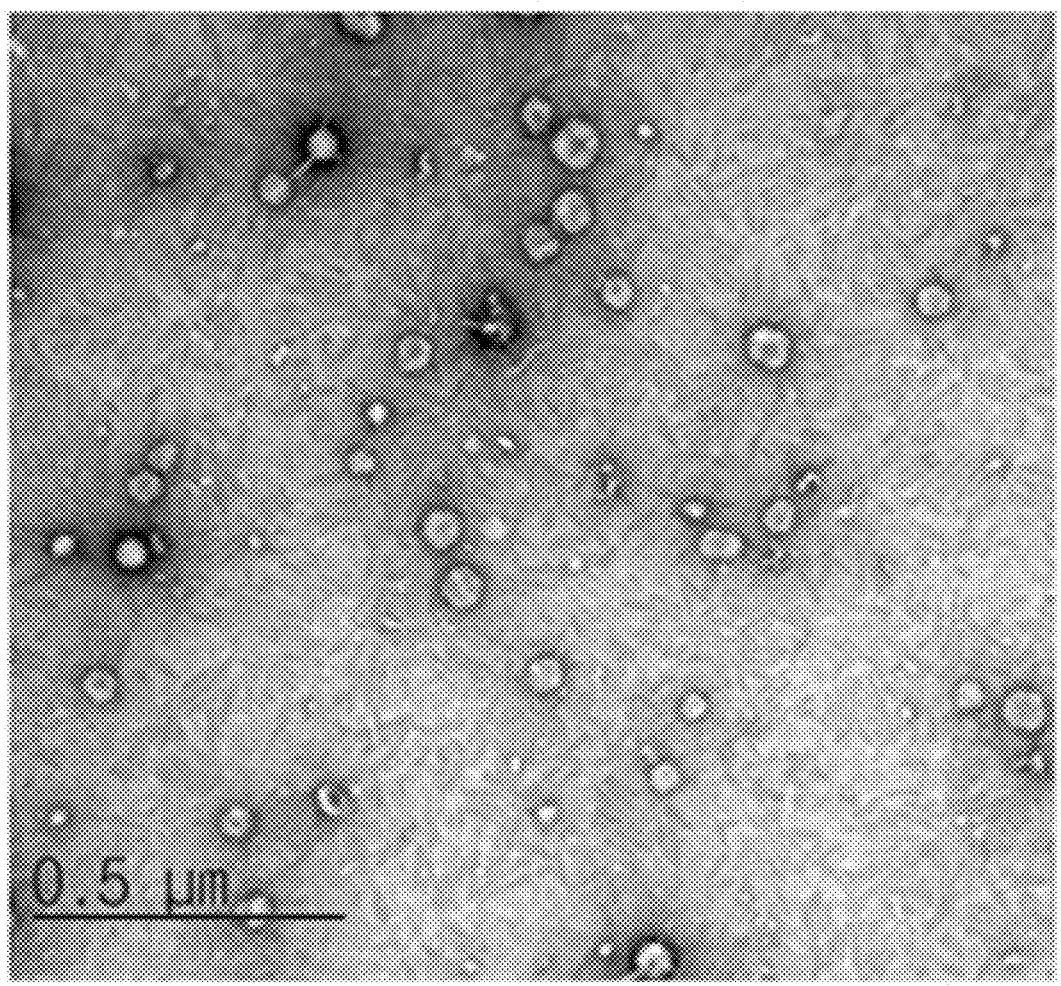

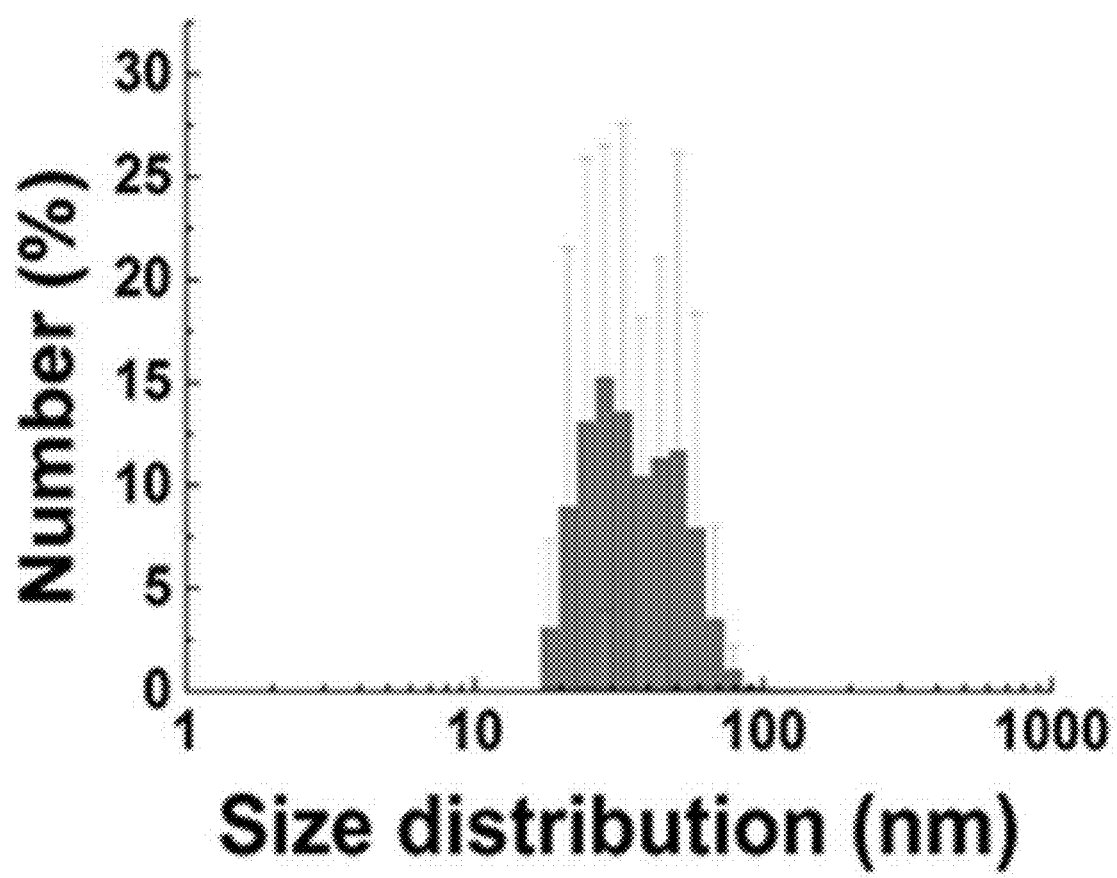
[Fig. 8B]

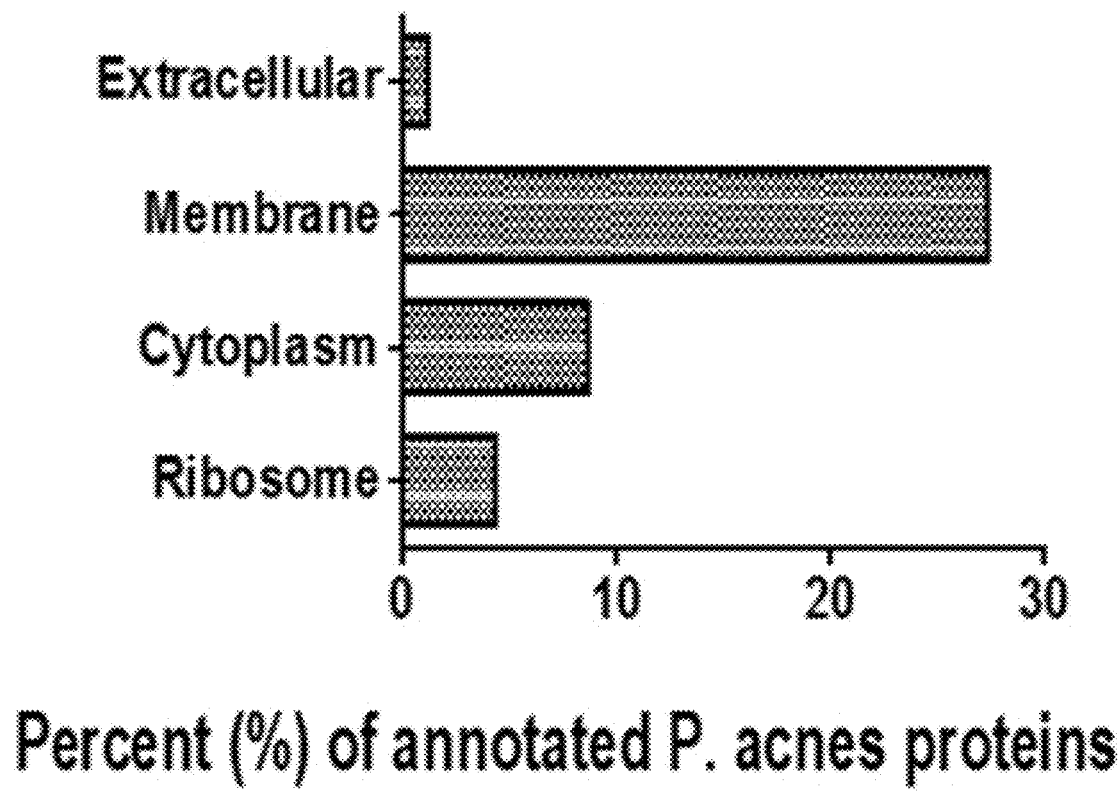
[Fig. 9A]

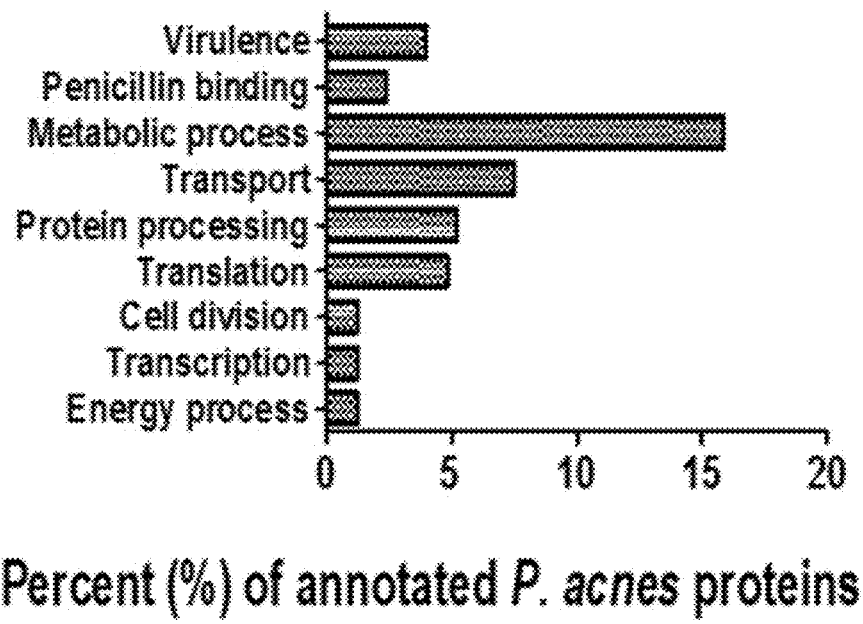
[Fig. 9B]

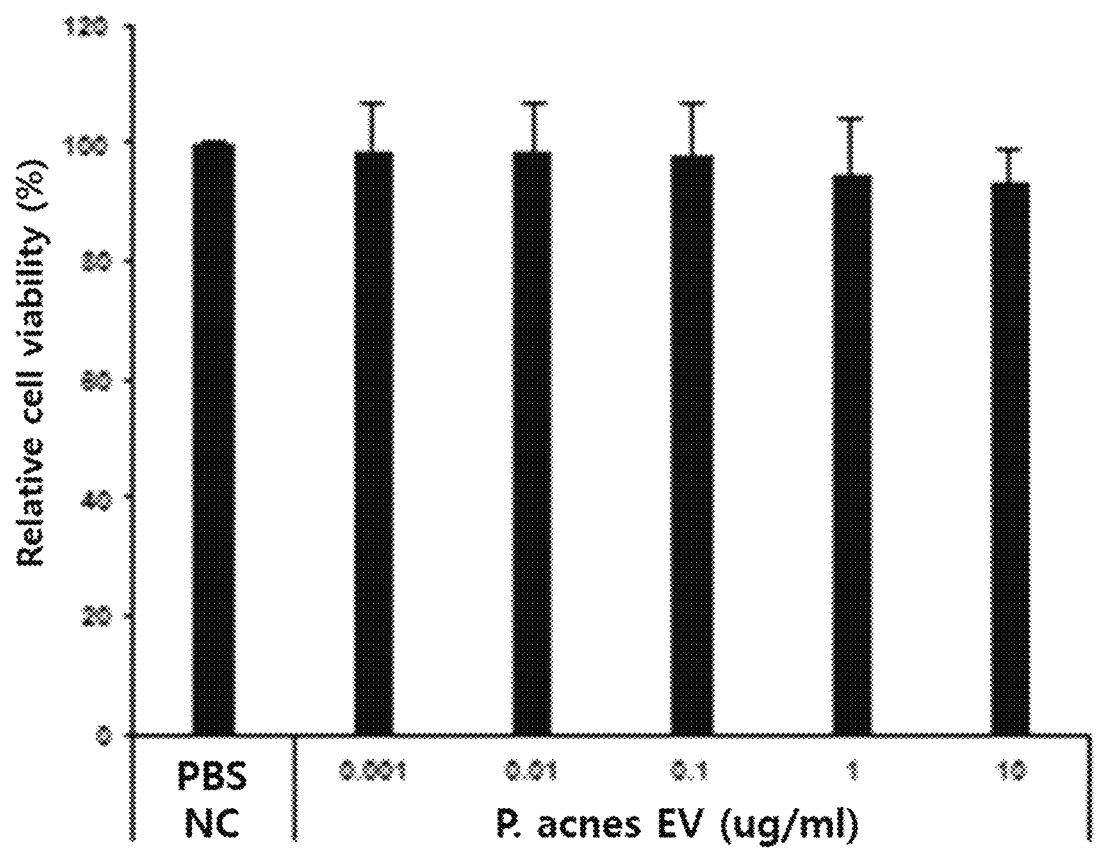
[Fig. 10A]

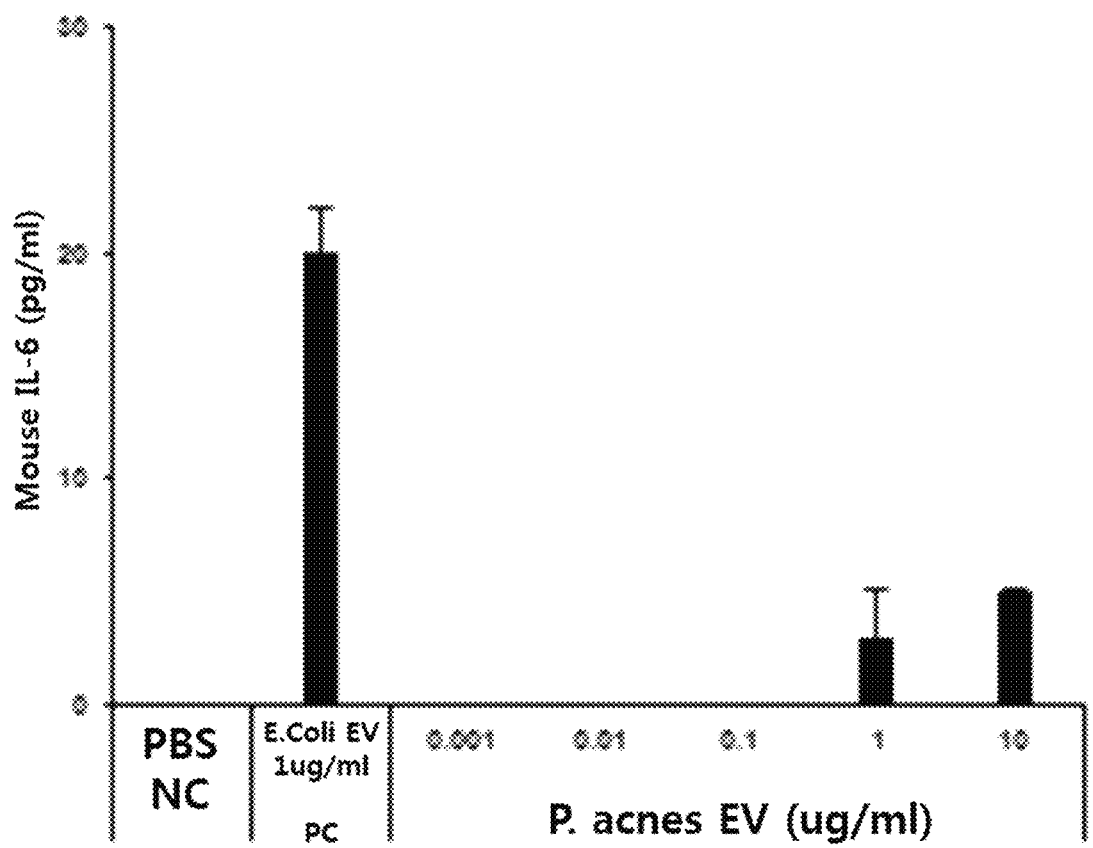
[Fig. 10B]

[Fig. 11A]
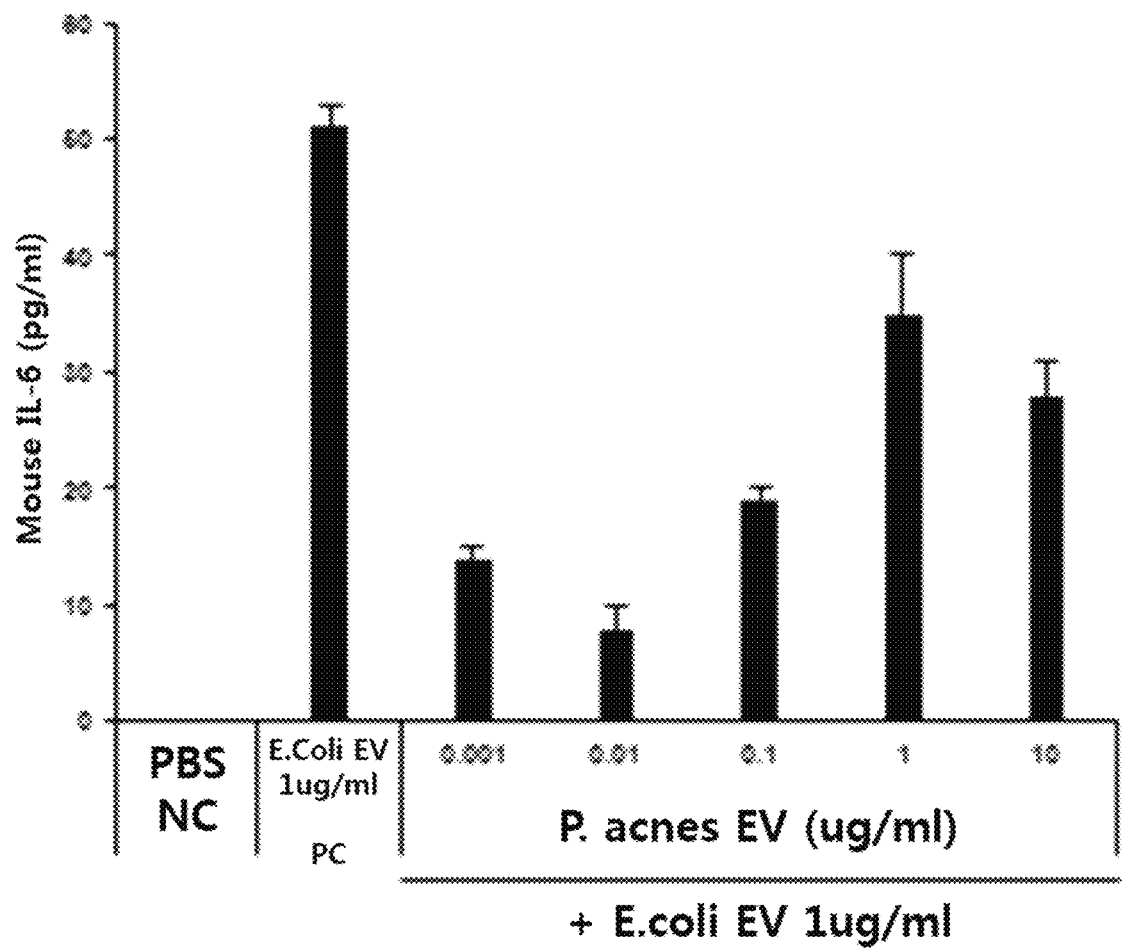

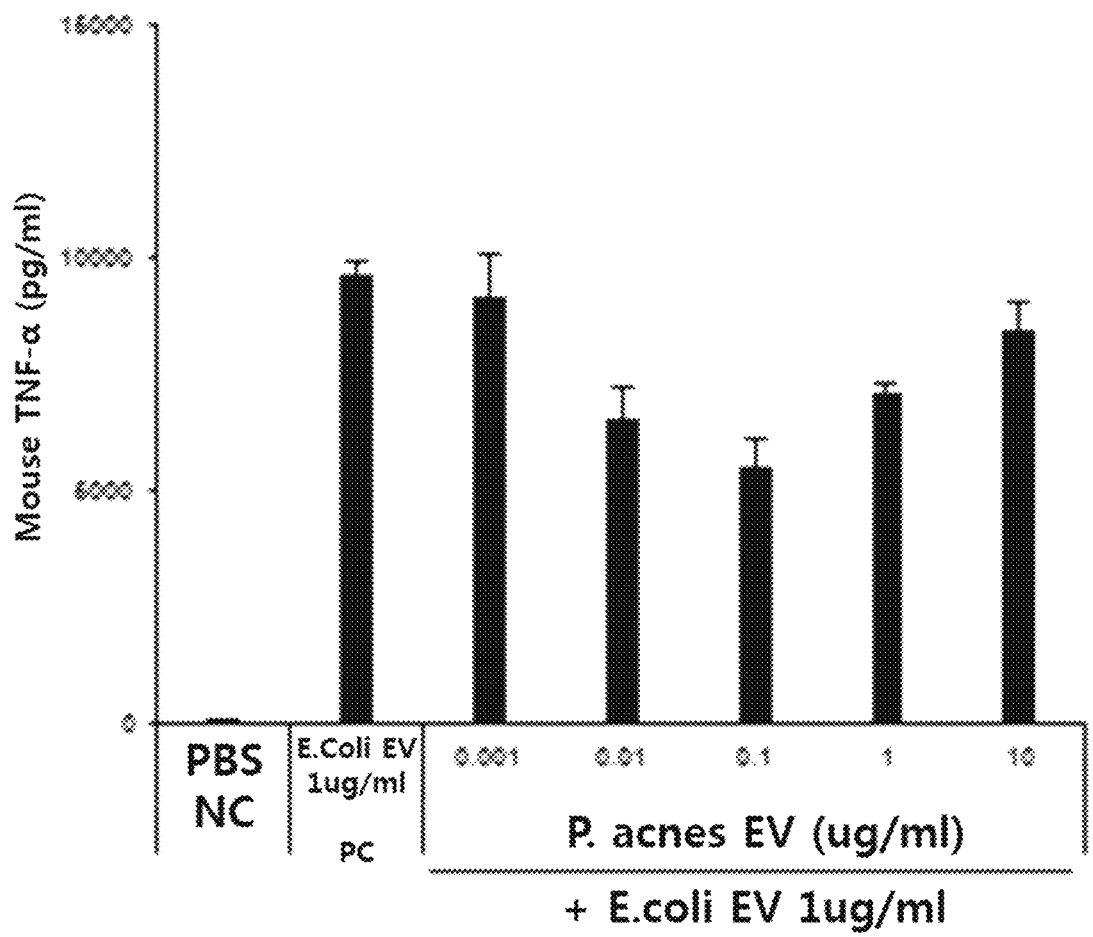
[Fig. 11B]

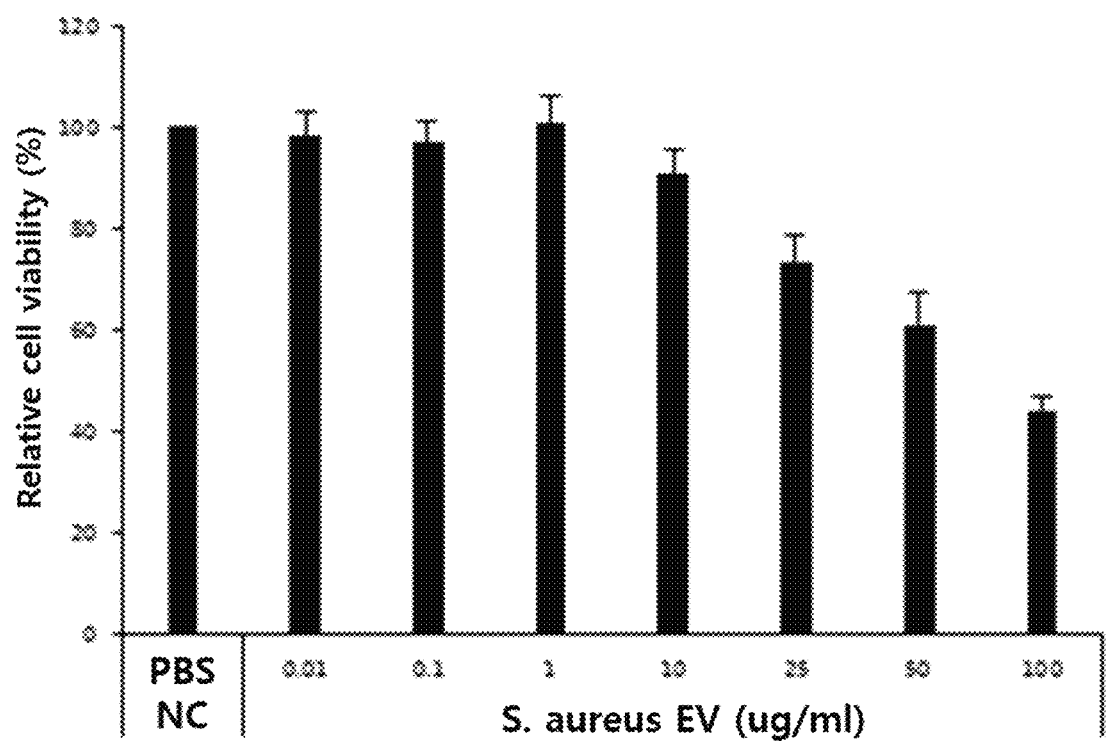
[Fig. 12A]

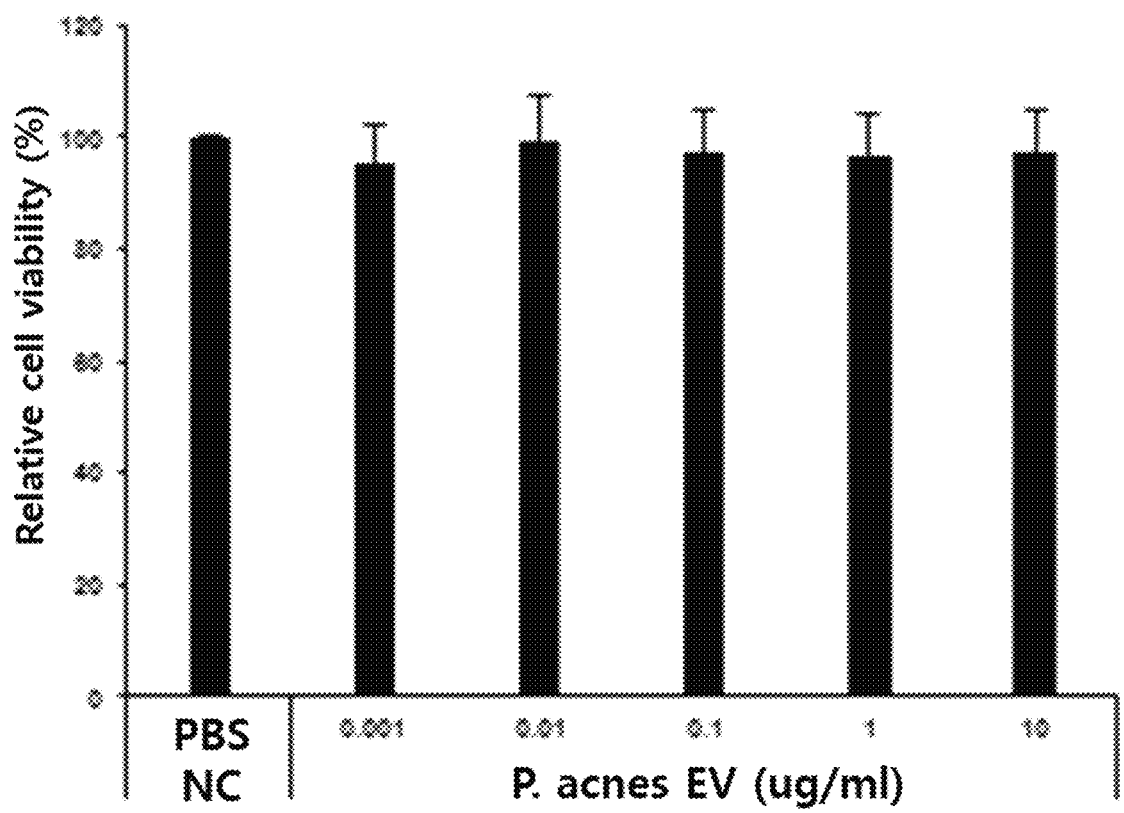
[Fig. 12B]

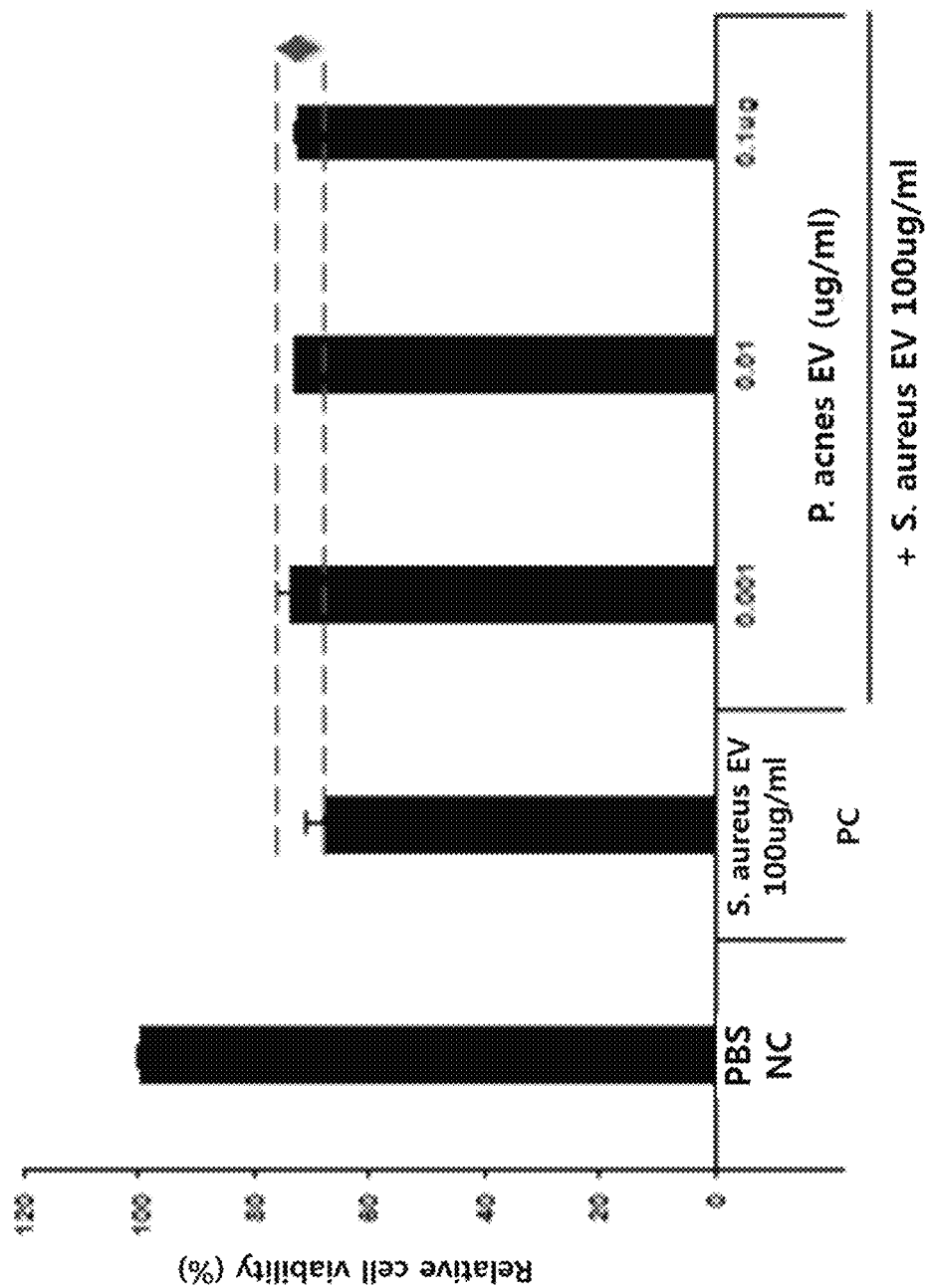
[Fig. 13]

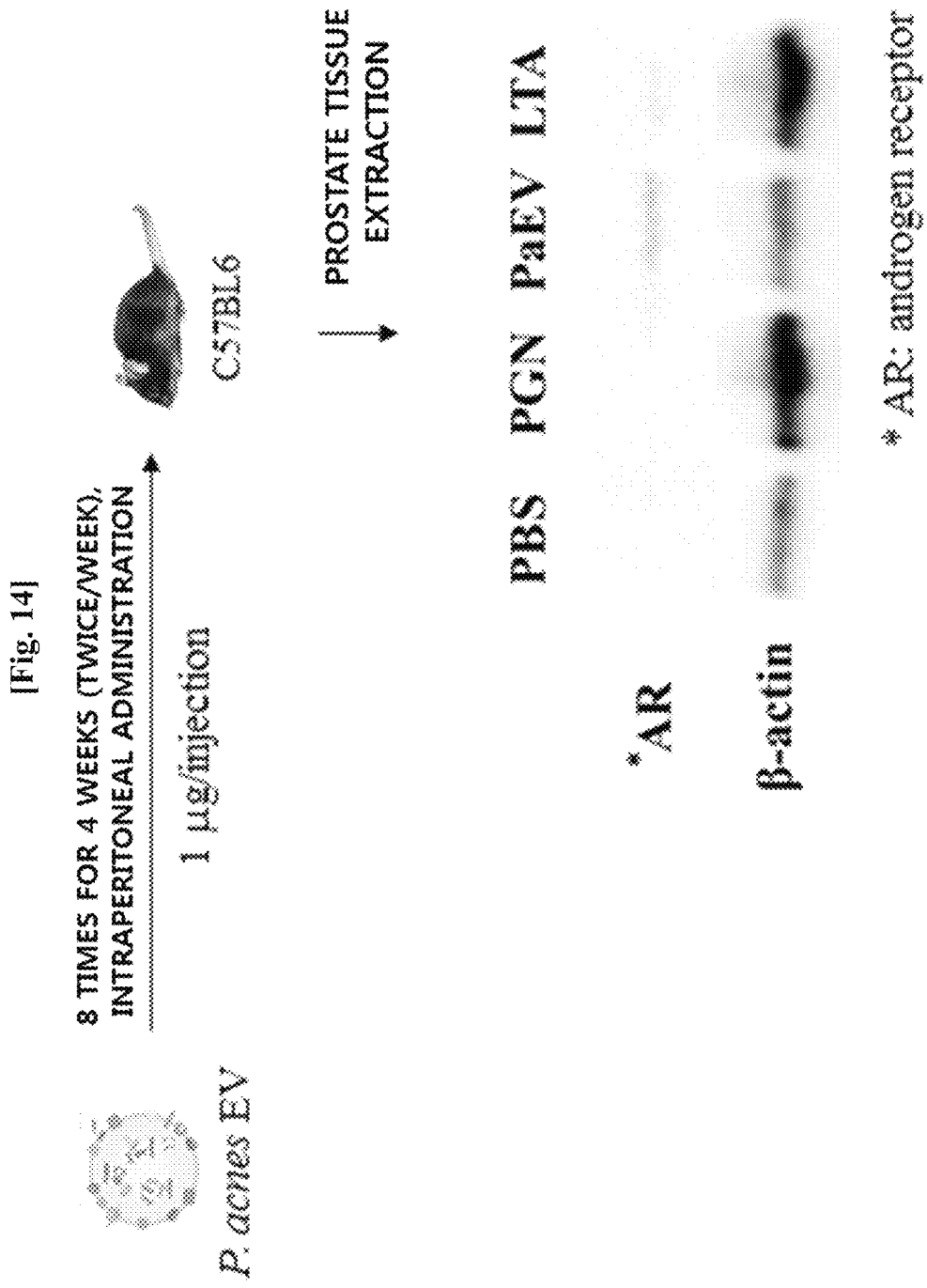

SEQUENCE LISTING

```
<160> NUMBER OF SEQ ID NOS: 2

<210> SEQ ID NO 1
<211> LENGTH: 50
<212> TYPE: DNA
<213> ORGANISM: Artificial Sequence
<220> FEATURE:
<223> OTHER INFORMATION: Forward primer for 16s rDNA
<220> FEATURE:
<221> NAME/KEY: misc_feature
<222> LOCATION: (42)..(42)
<223> OTHER INFORMATION: any nucleotide
<220> FEATURE:
<221> NAME/KEY: misc_feature
<222> LOCATION: (46)..(46)
<223> OTHER INFORMATION: a or t

<400> SEQUENCE: 1
tcgtcggcag cgtcagatgt gtataagaga cagcctacgg gnggcwgcag                50

<210> SEQ ID NO 2
<211> LENGTH: 55
<212> TYPE: DNA
<213> ORGANISM: Artificial Sequence
<220> FEATURE:
<223> OTHER INFORMATION: Reverse primer for 16s rDNA
<220> FEATURE:
<221> NAME/KEY: misc_feature
<222> LOCATION: (41)..(41)
<223> OTHER INFORMATION: a, c, or t
<220> FEATURE:
<221> NAME/KEY: misc_feature
<222> LOCATION: (42)..(42)
```

```
<223> OTHER INFORMATION: a c or g

<400> SEQUENCE: 2
gtctcgtggg ctcggagatg tgtataagag acaggactac hvgggtatct aatcc          55
```

NANO-VESICLES DERIVED FROM BACTERIA OF GENUS *PROPIONIBACTERIUM* AND USE THEREOF

STATEMENT REGARDING GOVERNMENT RIGHTS

The present invention was undertaken with the support of 1) Diagnostics and therapeutics development for immune and metabolic disease using human microbial vesicles No. NRF-2016M3A9B6901516 grant funded by the National Research Foundation of Korea 2) Stratified Medicine for Allergic Asthma based on Subtype Diagnosis No. HI14C2628 grant funded by the Ministry of Health & Welfare, Republic of Korea, 3) Point-of-care testing kit for the differential diagnosis of subtropical infectious diseases based on aptamer technology No. NRF-2014K1B1A1073720 grant funded by the National Research Foundation of Korea.

CROSS-REFERENCE TO RELATED APPLICATIONS

This application is the U.S. national phase filed under 35 U.S.C. § 371 claiming benefit to International Patent Application No. PCT/KR2017/006889, filed Jun. 29, 2017, which is entitled priority under 35 U.S.C. § 119(e) to Korean Application Serial No. 10-2016-0087058, filed Jul. 8, 2016 and Korean Application Serial No. 10-2017-0081782, filed Jun. 28, 2017, the disclosure of which is incorporated herein by reference in its entirety.

TECHNICAL FIELD

The present invention relates to nanovesicles derived from bacteria belonging to the genus *Propionibacterium* and a use thereof, and more particularly, to a method of diagnosing cancer, inflammatory diseases, endocrine diseases, or metabolic diseases by using nanovesicles derived from bacteria belonging to the genus *Propionibacterium*, and a preventive or therapeutic composition including the nanovesicles.

BACKGROUND ART

In the $21^{st}$ century, the importance of acute infectious diseases, which have been recognized as epidemics in the past, has become less important. On the other hand, chronic diseases accompanied by immune dysfunction occurring due to incompatibility of humans and a microbiome, especially cancer, cardiovascular diseases, chronic lung diseases, metabolic diseases, neuropsychiatric disorders, and the like, are becoming big issues in the $21^{st}$ century.

It is known that the number of microorganisms symbiotically living in the human body is 100 trillion which is 10 times that of human cells, and the number of genes of microorganisms exceeds 100 times that of humans. A microbiota or microbiome refers to a microbial community including bacteria, archaea, and eukarya present in a given habitat, and the intestinal microbiota is known to play a vital role in human physiological phenomena and significantly affect human health and diseases through interactions with human cells.

Bacteria living in the human body secrete nanometer-sized vesicles to exchange information about genes, proteins, and the like with other cells. The mucous membranes form a physical barrier membrane that does not allow particles with the size of 200 nm or more to pass therethrough, and thus bacteria symbiotically living in the mucous membranes are unable to pass therethrough, but bacterial-derived vesicles have a size of approximately 100 nm or less and thus relatively freely pass through the mucous membranes and are absorbed into the human body. Pathogenic bacteria-derived vesicles that are absorbed into the body have turned out to be an important factor in the causes of inflammatory diseases, such as inflammatory skin diseases such as atopic dermatitis, inflammatory respiratory diseases such as chronic rhinitis, asthma, chronic obstructive pulmonary disease (COPD), and the like, and inflammatory bowel diseases such as ulcerative colitis, Crohn's disease, and the like. In addition, it has recently been found that pathogenic bacteria-derived vesicles are closely associated with the onset of metabolic diseases such as diabetes, obesity, and the like, and solid cancer such as liver cancer, stomach cancer, colorectal cancer, and the like, and they are attracting attention.

Bacteria belonging to the genus *Propionibacterium* are anaerobic Gram-positive bacilli and are characterized by the synthesis of propionic acid through a transcarboxylase. The bacteria are known to be bacteria that symbiotically live with animals including humans and also symbiotically live not only in the skin but also in the gastrointestinal tract. In most cases, the bacteria do not cause diseases, but it is known that *Propionibacterium acnes* (acne bacteria) uses, as an energy source, fatty acids present in sebum secreted from the sebaceous glands, and is the most important causative bacterium in skin diseases such as acne. Bacteria belonging to the genus *Propionibacterium* are industrially used in the synthesis of vitamin B12, tetrapyrrole compounds, and propionic acid, probiotics, cheese production, and the like. To date, the fact that bacteria belonging to the genus *Propionibacterium* extracellularly secrete vesicles has not been reported, and studies have been carried out only on the use of *Propionibacterium*, preferably *P. freudenreichii*, which is a congeneric and heterogeneous species of *Propionibacterium acnes* in the treatment of allergies, influenza vaccines, and gastrointestinal dysfunction (see JP 2016-028033 and KR 10-1459166).

Meanwhile, androgen receptors are intracellular receptors that bind to male hormones such as testosterone, dihydrotestosterone, and the like and play a vital role in an increase in muscle mass and bone density, and the expression and maintenance of male phenotypes, such as hair growth. In addition, male hormones are known to play an important role in the prevention of osteoporosis, frailty, and the like through an androgen receptor.

Therefore, the inventors of the present invention confirmed that the amount of vesicles derived from bacteria belonging to the genus *Propionibacterium* was reduced in blood samples of patients with cancer, chronic inflammatory diseases, endocrine diseases, and metabolic diseases, as compared to that of normal people, and thus completed the present invention based on these findings.

DISCLOSURE

Technical Problem

The inventors of the present invention isolated vesicles from bacteria belonging to the genus *Propionibacterium* for the first time and confirmed the characteristics thereof, and thus confirmed that the vesicles could be used as a composition for the prevention or treatment of cancer, inflammatory diseases, endocrine diseases, or metabolic diseases.

Specifically, it was confirmed through metagenomic analysis that the amount of vesicles derived from bacteria belonging to the genus *Propionibacterium* was significantly reduced in samples derived from patients with cancer such as liver cancer, breast cancer, and the like, and inflammatory or metabolic diseases such as atopic dermatitis, asthma, diabetes, liver cirrhosis, and the like, as compared to that of normal people. As a result of isolating vesicles derived from bacteria belonging to the genus *Propionibacterium* in vitro and evaluating therapeutic efficacy thereof, it was confirmed that the vesicles exhibited an anti-inflammatory effect and an effect of inhibiting the death of keratinocytes, and as a result of evaluating the mechanism of the vesicles, it was confirmed that the vesicles increased the expression of male hormone receptors, thus completing the present invention based on these findings.

Therefore, an object of the present invention is to provide a method of providing information for the diagnosis of cancer, inflammatory diseases, endocrine diseases, or metabolic diseases.

Another object of the present invention is to provide a composition for alleviating or treating cancer, an inflammatory disease, an endocrine disease, or a metabolic disease, which includes, as an active ingredient, vesicles derived from bacteria belonging to the genus *Propionibacterium*.

However, technical problems to be solved by the present invention are not limited to the above-described technical problems, and other unmentioned technical problems will become apparent from the following description to those of ordinary skill in the art.

Technical Solution

To achieve the above-described objects of the present invention, the present invention provides a method of providing information for the diagnosis of cancer, an inflammatory disease, an endocrine disease, or a metabolic disease, the method including the following processes:

(a) extracting DNA from vesicles isolated from normal people-derived samples or patient-derived samples;

(b) performing PCR on the extracted DNAs by using a pair of primers for detecting vesicles derived from bacteria belonging to the genus *Propionibacterium* present in a 16S rDNA sequence; and (c) determining a case, in which the amount of vesicles derived from bacteria belonging to the genus *Propionibacterium* is lower than that of normal people, as cancer, an inflammatory disease, an endocrine disease, or a metabolic disease, through quantitative analysis of the PCR products.

In one embodiment of the present invention, the patient-derived sample may be blood or urine.

The present invention also provides a pharmaceutical composition for preventing or treating cancer, an inflammatory disease, an endocrine disease, or a metabolic disease, which includes, as an active ingredient, vesicles derived from bacteria belonging to the genus *Propionibacterium*.

In one embodiment of the present invention, the bacteria belonging to the genus *Propionibacterium* may be *Propionibacterium acnes*.

In another embodiment of the present invention, the vesicles may have an average diameter of 10 nm to 1,000 nm.

In another embodiment of the present invention, the vesicles may be naturally or artificially secreted from bacteria belonging to the genus *Propionibacterium*.

In another embodiment of the present invention, the patient-derived samples may be urine or blood.

In another embodiment of the present invention, the composition may be an inhalant.

In another embodiment of the present invention, the composition may use a protein included in vesicles derived from *Propionibacterium acnes*.

In another embodiment of the present invention, the cancer may be liver cancer or breast cancer.

In another embodiment of the present invention, the inflammatory disease may be atopic dermatitis, asthma, diabetes, or liver cirrhosis.

In another embodiment of the present invention, the endocrine disease may be osteoporosis, frailty, or hair loss.

In another embodiment of the present invention, the metabolic disease may be diabetes or liver cirrhosis.

The present invention also provides a food composition for preventing or alleviating cancer, an inflammatory disease, an endocrine disease, or a metabolic disease, which includes, as an active ingredient, vesicles derived from bacteria belonging to the genus *Propionibacterium*.

The present invention also provides a cosmetic composition for alleviating cancer, an inflammatory disease, an endocrine disease, or a metabolic disease, which includes, as an active ingredient, vesicles derived from bacteria belonging to the genus *Propionibacterium*.

The present invention also provides a method of preventing or treating cancer, an inflammatory disease, an endocrine disease, or a metabolic disease, which includes administering, to an individual, a pharmaceutical composition including, as an active ingredient, vesicles derived from bacteria belonging to the genus *Propionibacterium*.

The present invention also provides a use of a pharmaceutical composition including, as an active ingredient, vesicles derived from bacteria belonging to the genus *Propionibacterium* for the prevention or treatment of cancer, an inflammatory disease, an endocrine disease, or a metabolic disease.

Advantageous Effects

The inventors of the present invention confirmed that the amount of vesicles derived from bacteria belonging to the genus *Propionibacterium* was increased in high fat dietary mice-derived stool samples compared to regular CHO dietary mice, thus confirming an increase in the activity of bacteria belonging to the genus *Propionibacterium* by fat, and confirmed through metagenomic analysis of vesicles derived from bacteria present in blood samples of patients that vesicles derived from bacteria belonging to the genus *Propionibacterium* present in blood samples of patients with liver cancer, breast cancer, asthma, atopic dermatitis, diabetes, and liver cirrhosis, was significantly reduced as compared to that of normal people. In addition, it was experimentally confirmed that, when vesicles isolated from in vitro cultured *Propionibacterium acnes*, which is one species of bacteria belonging to the genus *Propionibacterium*, was administered to mice, the expression of an androgen receptor in prostate tissues was increased, and it was observed that, when inflammatory cells were pretreated with the vesicles, the vesicles had an anti-inflammatory effect and an immune regulatory effect. Accordingly, the vesicles derived from bacteria belonging to the genus *Propionibacterium*, according to the present invention, are expected to be usefully used in a method of diagnosing or predicting cancer, an inflammatory disease, an endocrine disease, or a metabolic disease, a pharmaceutical composition, a food, a cosmetic, and the like.

DESCRIPTION OF DRAWINGS

FIG. 1 depicts a protocol for metagenomic analysis of vesicles isolated from the stool of mice fed a regular CHO diet (RCD) or a high fat diet (HFD).

FIG. 2 illustrates metagenomic analysis results of bacteria and vesicles, isolated from the stool of mice fed a regular CHO diet (RCD) and a 12-week-long high fat diet (HFD).

FIG. 3A illustrates images showing distribution patterns of intestinal bacteria and bacteria-derived vesicles (EV) according to time after being orally administered to mice.

FIG. 3B illustrates images showing evaluation results of in vivo distribution patterns of bacteria and vesicles in blood, kidneys, and various organs that were extracted at 12 hours after oral administration.

FIG. 4 is a diagram illustrating a method of performing metagenomic analysis on vesicles derived from bacteria present in the human body.

FIG. 5A illustrates results of comparing distribution patterns of vesicles derived from bacteria belonging to the genus Propionibacterium after metagenomic analysis was performed on vesicles derived from bacteria present in blood samples of patients with liver cancer and normal people with age and gender matched with those of the patients.

FIG. 5B illustrates results of comparing distribution patterns of vesicles derived from bacteria belonging to the genus Propionibacterium after metagenomic analysis was performed on vesicles derived from bacteria present in blood samples of patients with breast cancer and normal people with age and gender matched with those of the patients.

FIG. 6A illustrates results of comparing distribution patterns of vesicles derived from bacteria belonging to the genus Propionibacterium after metagenomic analysis was performed on vesicles derived from bacteria present in blood samples of patients with asthma and normal people with age and gender matched with those of the patients.

FIG. 6B illustrates results of comparing distribution patterns of vesicles derived from bacteria belonging to the genus Propionibacterium after metagenomic analysis was performed on vesicles derived from bacteria present in blood samples of patients with atopic dermatitis and normal people with age and gender matched with those of the patients.

FIG. 7A illustrates results of comparing distribution patterns of vesicles derived from bacteria belonging to the genus Propionibacterium after metagenomic analysis was performed on vesicles derived from bacteria present in blood samples of patients with diabetes and normal people with age and gender matched with those of the patients.

FIG. 7B illustrates results of comparing distribution patterns of vesicles derived from bacteria belonging to the genus Propionibacterium after metagenomic analysis was performed on vesicles derived from bacteria present in blood samples of patients with liver cirrhosis and normal people with age and gender matched with those of the patients.

FIG. 8A is an electron microscope image showing observation results of the shape of vesicles isolated from a culture solution obtained by culturing Propionibacterium acnes in vitro.

FIG. 8B illustrates results of measuring the size of vesicles isolated from a Propionibacterium acnes culture solution by dynamic light scattering.

FIG. 9A illustrates results of classifying identified proteins obtained as a result of analyzing proteomes included in Propionibacterium acnes-derived vesicles, according to cellular components.

FIG. 9B illustrates results of classifying identified proteins obtained as a result of analyzing proteomes included in Propionibacterium acnes-derived vesicles, according to functions.

FIG. 10A illustrates results of measuring the degree of apoptosis of Propionibacterium acnes-derived vesicles after a macrophage line was treated therewith.

FIG. 10B illustrates results of measuring the secretion of IL-6, which is an inflammatory mediator, of Propionibacterium acnes-derived vesicles after a macrophage line was treated therewith.

FIG. 11A illustrates results of evaluating an effect of E. coli vesicles (E. coli EV) on the secretion of IL-6, which is an inflammatory mediator, when a macrophage was pre-treated with Propionibacterium acnes-derived vesicles at various concentrations, and then was treated with the E. coli vesicles, which are pathogenic vesicles.

FIG. 11B illustrates results of evaluating an effect of E. coli vesicles (E. coli EV) on the secretion of TNF-α, which is an inflammatory mediator, when a macrophage was pretreated with Propionibacterium acnes-derived vesicles at various concentrations, and then was treated with the E. coli vesicles, which are pathogenic vesicles.

FIG. 12A illustrates results of evaluating the degree of apoptosis of keratinocytes by S. aureus-derived vesicles (S. aureus EV), after skin keratinocytes were treated with S. aureus-derived vesicles at various concentrations.

FIG. 12B illustrates results of evaluating the degree of apoptosis of keratinocytes by Propionibacterium acnes-derived vesicles (P. acnes EV), after skin keratinocytes were treated with Propionibacterium acnes-derived vesicles at various concentrations.

FIG. 13 illustrates results of measuring the apoptosis of keratinocytes after the keratinocytes were pretreated with Propionibacterium acnes-derived vesicles (P. acnes EV) at various concentrations, and then treated with a high concentration of S. aureus-derived vesicles (S. aureus EV), in order to evaluate an inhibitory effect of the Propionibacterium acnes-derived vesicles on skin death caused by S. aureus-derived vesicles, which are pathogenic vesicles of skin diseases.

FIG. 14 illustrates results of evaluating the expression pattern of an androgen receptor in prostate tissue by western blotting, after Propionibacterium acnes-derived vesicles were intraperitoneally administered to mice 8 times for 4 weeks.

BEST MODE

The present invention relates to vesicles derived from bacteria belonging to the genus Propionibacterium and a use thereof.

The inventors of the present invention had confirmed through metagenomic analysis that the amount of vesicles derived from bacteria belonging to the genus Propionibacterium was significantly reduced in samples derived from patients with cancer such as liver cancer, breast cancer, and the like, inflammatory diseases such as atopic dermatitis, asthma, and the like, and endocrine or metabolic diseases such as diabetes, liver cirrhosis, and the like, as compared to that of normal people, and thus completed the present invention based on these findings.

Therefore, the present invention provides a method of providing information for the diagnosis of cancer, an inflammatory disease, an endocrine disease, or a metabolic disease, the method including the following processes:

(a) extracting DNA from vesicles isolated from normal people-derived samples or patient-derived samples;

(b) performing PCR on the extracted DNAs by using a pair of primers for detecting vesicles derived from bacteria belonging to the genus *Propionibacterium* present in a 16S rDNA sequence; and (c) determining a case, in which the amount of vesicles derived from bacteria belonging to the genus *Propionibacterium* is lower than that of normal people, as cancer, an inflammatory disease, an endocrine disease, or a metabolic disease, through quantitative analysis of the PCR products.

The term "diagnosis" as used herein means, in a broad sense, determining conditions of disease of a patient in all aspects. Content of the determination includes disease name, the cause of a disease, the type of disease, the severity of disease, detailed aspects of syndrome, the presence or absence of complications, prognosis, and the like. In the present invention, diagnosis means determining the presence or absence of the onset of cancer, an inflammatory disease, or a metabolic disease, the severity of disease, and the like.

The term "cancer," which is a diagnostic target disease of the present invention, means malignant tumors that grow rapidly while infiltrating into the surrounding tissues and diffuse or transit to each part of the body, and thus are life-threatening. Cells, which are the smallest unit of the body, normally divide and grow by the regulatory function of cells themselves, and when the lifespan of cells end or cells get damaged, they themselves die and thus maintain a balance in an overall number of cells. However, when cells have a problem with such a regulatory function thereof, due to various causes, abnormal cells, which would normally die, excessively proliferate, and infiltrate into the surrounding tissues and organs to thereby form a mass, resulting in destruction or modification of existing structures. In the present invention, the cancer may be, but is not limited to, preferably liver cancer or breast cancer.

The term "inflammatory disease" as used herein refers to a disease caused by an inflammatory reaction in the mammalian body, and representative examples thereof include respiratory inflammatory diseases such as asthma, chronic obstructive pulmonary disease, rhinitis, and the like; skin inflammatory diseases such as atopic dermatitis, psoriasis, acne, contact dermatitis, and the like; gastrointestinal inflammatory diseases such as gastritis, digestive ulcers, inflammatory bowel disease, and the like; and complications of the above-listed diseases. In addition, the term "inflammatory disease" is used as including inflammatory reaction-related cancer, in addition to general inflammatory diseases, for example, lung cancer, stomach cancer, colorectal cancer, and the like. In the present invention, the inflammatory disease is preferably asthma or atopic dermatitis, but the present invention is not limited thereto.

The term "endocrine disease" as used herein refers to disorder caused by excessive or deficient hormones in the mammalian body, and examples thereof include breast cancer occurring due to excessive female hormones, osteoporosis due to a reduction in male hormones, frailty, hair loss, and the like. In the present invention, the endocrine disease preferably includes, but is not limited to, osteoporosis, frailty, or hair loss.

The term "metabolic disease" as used herein refers to a disease caused by metabolic disorders and complications thereof in the mammalian body, and examples thereof include hyperlipidemia due to a lipid metabolism abnormality, diabetes due to a carbohydrate metabolism abnormality, liver cirrhosis occurring as a result of complications of metabolic disorders, and the like. In the present invention, the metabolic disease preferably includes, but is not limited to, diabetes or liver cirrhosis.

The term "nanovesicles" or "vesicles" as used herein refers to structures consisting of nano-sized membranes secreted by various bacteria. Gram-negative bacteria-derived EVs, or outer membrane vesicles (OMVs) contain lipopolysaccharides, toxic proteins, and bacterial DNA and RNA, and gram-positive bacteria-derived EVs also contain peptidoglycan and lipoteichoic acid, which are cell wall components of bacteria, in addition to proteins and nucleic acids. In the present invention, nanovesicles or vesicles are naturally secreted or artificially produced in bacteria belonging to the genus *Propionibacterium*, and have a spherical shape and an average diameter of 10 nm to 1,000 nm.

The vesicles may be isolated from a culture solution containing bacteria belonging to the genus *Propionibacterium* by using one or more methods selected from centrifugation, ultracentrifugation, extrusion, ultrasonic degradation, cell lysis, homogenization, freezing-thawing, electroporation, mechanical degradation, chemical treatment, filtration using a filter, gel filtration chromatography, free-flow electrophoresis, and capillary electrophoresis. In addition, the isolation methods may further include washing for the removal of impurities, concentration of obtained vesicles, and the like.

The term "metagenome" as used herein refers to the total of genomes including all viruses, bacteria, fungi, and the like in isolated regions such as soil, the intestines of animals, and the like, and is mainly used as a concept of genomes that explains identification of many microorganisms at one time using a sequencer to analyze non-cultured microorganisms. In particular, a metagenome does not refer to a genome of one species, but refers to a mixture of genomes, including genomes of all species of an environmental unit. This term originates from the view that, when defining one species in a process in which biology is advanced into omics, various species as well as an existing one species functionally interact with each other to form a complete species. Technically, it is the subject of techniques that analyze all DNAs and RNAs regardless of species using rapid sequencing to identify all species in one environment and verify interactions and metabolism.

In the present invention, the patient-derived samples may be, but is not limited to, blood or urine.

According to another embodiment of the present invention, there is provided a pharmaceutical composition for preventing or treating cancer, an inflammatory disease, an endocrine disease, or a metabolic disease, which includes, as an active ingredient, vesicles derived from bacteria belonging to the genus *Propionibacterium*.

According to still another embodiment of the present invention, there is provided a food composition for preventing or alleviating cancer, an inflammatory disease, an endocrine disease, or a metabolic disease, which includes, as an active ingredient, vesicles derived from bacteria belonging to the genus *Propionibacterium*.

According to yet another embodiment of the present invention, there is provided a cosmetic composition for alleviating cancer, an inflammatory disease, an endocrine disease, or a metabolic disease, which includes, as an active ingredient, vesicles derived from bacteria belonging to the genus *Propionibacterium*.

The term "prevention" as used herein means all actions that inhibit cancer, an inflammatory disease, an endocrine disease, or a metabolic disease or delay the onset thereof via administration of the food, inhalant, or pharmaceutical composition according to the present invention.

The term "treatment" as used herein means all actions that alleviate or beneficially change symptoms due to cancer, an inflammatory disease, an endocrine disease, or a metabolic disease via administration of the pharmaceutical composition according to the present invention.

The term "alleviation" as used herein means all actions that decrease at least the degree of parameters related to conditions in which cancer, an inflammatory disease, an endocrine disease, or a metabolic disease is being treated, e.g., symptoms via administration of the food or cosmetic composition according to the present invention.

In one embodiment of the present invention, it was confirmed that vesicles derived from bacteria belonging to the genus *Propionibacterium* was increased in the stool of mice fed a high fat diet, as high fat dietary animal models, as compared to the stool of mice fed a regular CHO diet (see Example 1).

In one embodiment of the present invention, bacterial metagenomic analysis was performed using vesicles isolated from blood samples of patients with breast cancer or liver cancer, and normal people. As a result, it was confirmed that vesicles derived from bacteria belonging to the genus *Propionibacterium* was significantly reduced in the blood samples of patients with breast cancer or liver cancer, as compared to that in the blood samples of normal people (see Example 3).

In one embodiment of the present invention, bacterial metagenomic analysis was performed using vesicles isolated from blood samples of patients with asthma or atopic dermatitis, and normal people. As a result, it was confirmed that vesicles derived from bacteria belonging to the genus *Propionibacterium* was significantly reduced in the blood samples of patients with asthma or atopic dermatitis, as compared to that in the blood samples of normal people (see Example 4).

In one embodiment of the present invention, bacterial metagenomic analysis was performed using vesicles isolated from blood samples of patients with diabetes or liver cirrhosis, and normal people. As a result, it was confirmed that vesicles derived from bacteria belonging to the genus *Propionibacterium* was significantly reduced in the blood samples of patients with diabetes or liver cirrhosis, as compared to that in the blood samples of normal people (see Example 5).

In another embodiment of the present invention, as a result of further having conducted studies to analyze the characteristics of vesicles derived from *Propionibacterium acnes*, which belongs to the genus *Propionibacterium*, on the basis of the results of Examples 3 to 5, it was confirmed that the vesicles had an average diameter of less than 200 nm and preferably had a spherical shape with a size of 37.8±13.5 nm (see Example 6).

In another embodiment of the present invention, 252 proteins present in *Propionibacterium acnes*-derived vesicles were identified through proteomic analysis, and were classified according to cellular components and protein functions (see Example 7).

In another embodiment of the present invention, as a result of evaluating an effect of vesicles isolated from a cultured strain of *Propionibacterium acnes* on the secretion of inflammatory mediators, the capability of the vesicles derived from *Propionibacterium acnes* to secrete IL-6 in a macrophage line was significantly lower than that of *E. coli*-derived vesicles (*E. coli* EV), which are pathogenic vesicles. In addition, as a result of evaluating the secretion of inflammatory mediators after macrophages were treated with *Propionibacterium acnes*-derived vesicles at various concentrations, and then treated with *E. coli* vesicles, which are a causative factor of inflammation and metabolic diseases, it was confirmed that the *Propionibacterium acnes*-derived vesicles efficiently inhibited the secretion of IL-6 and TNF-α due to the *E. coli*-derived vesicles (see Example 8).

In another embodiment of the present invention, as a result of evaluating an effect of vesicles isolated from a cultured strain of *Propionibacterium acnes* on the treatment of atopic dermatitis, it was confirmed that, when skin keratinocytes were pretreated with *Propionibacterium acnes*-derived vesicles before being treated with *Staphylococcus aureus*-derived vesicles (*Staphylococcus aureus* EV), which are an important causative factor for atopic dermatitis, the *Propionibacterium acnes*-derived vesicles inhibited the death of keratinocytes due to *Staphylococcus aureus*-derived vesicles (see Example 9).

In another embodiment of the present invention, as a result of analyzing prostate tissues extracted after the *Propionibacterium acnes*-derived vesicles were administered to mice to evaluate an effect of the *Propionibacterium acnes*-derived vesicles on the expression of male hormone receptors, which is one of the therapeutic mechanisms for endocrine diseases, it was confirmed that in the case in which the vesicles were administered, the expression of androgen receptors was increased in the prostate tissues (see Example 10).

Hereinafter, exemplary examples will be described to aid in understanding of the present invention. However, the following examples are provided only to facilitate the understanding of the present invention and are not intended to limit the scope of the present invention.

EXAMPLES

Example 1. Metagenomic Analysis of Bacteria and Bacteria-Derived Vesicles in Stool of Mice Fed Regular CHO Diet and High Fat Diet Stool was collected from normal mice fed a regular CHO diet (RCD) for 12 weeks and mice fed a high fat diet (HFD) for 2 months to thereby induce obesity, according to the method illustrated in FIG. 1. Subsequently, the weight (gram) of the collected mouse stool was measured and dispersed in PBS. To remove impurities, each stool sample was sequentially centrifuged at 500×g for 5 minutes, at 3,000×g for 5 minutes, and at 4,350 rpm for 5 minutes to separate a supernatant, and then was ultracentrifuged at 10,000×g for 20 minutes to separate bacteria included in the stool. In addition, to isolate vesicles, the bacteria-removed supernatant was filtered using a 0.45 μm filter, and then proteins were quantified. Thereafter, 0.8 M and 2.5 M sucrose cushions were prepared and subjected to ultrahigh speed centrifugation twice at 28,500 rpm and 4° C. for 2 hours, followed by ultrahigh speed centrifugation at 40,200 rpm and 4° C. for 2 hours to obtain stool-derived vesicles, and the obtained vesicles were dispersed in PBS and stored.

100 μl of the bacteria and the vesicles, separated using the above-described method, were boiled at 100° C. to release internal DNA out of the lipid, and then cooled on ice for 5 minutes. Then, to remove the remaining floating materials, the resultant samples were centrifuged at 10,000×g and 4° C.

for 30 minutes to collect only supernatants. The amounts of DNAs were then quantified using Nanodrop. Subsequently, PCR was performed on the extracted DNAs using a pair of 16S rRNA primers shown in Table 1 below to confirm the presence or absence of bacteria-derived DNA, thereby confirming the presence of bacteria-derived genes in the extracted DNAs.

TABLE 1

| | primer | sequence | SEQ ID NO. |
|---|---|---|---|
| 16S rDNA | 16S_V3_F | 5'-TCGTCGGCAGCG TCAGATGTGTATAAG AGACAGCCTACGGGN GGCWGCAG-3' | 1 |
| | 16S_V4_R | 5'-GTCTCGTGGGCT CGGAGATGTGTATAA GAGACAGGACTACHV GGGTATCTAATCC-3' | 2 |

The DNAs extracted using the above method were amplified using the pair of 16S rDNA primers, and then sequenced (Illumina MiSeq sequencer), the results were output in the form of a Standard Flowgram Format (SFF) file and the SFF file was converted into a sequence file (.fasta) and a nucleotide quality score file by using GS FLX software (v2.9), and then a reliability estimation for reads was identified and a portion with a window (20 bps) average base call accuracy of less than 99% (Phred score<20) was removed. For operational taxonomy unit (OTU) analysis, clustering was performed according to the sequence similarity using UCLUST and USEARCH, the genus, family, order, class, and phylum were clustered based on the sequence similarities of 94%, 90%, 85%, 80%, and 75%, respectively, levels of the phylum, class, order, family, and genus of respective OTUs were classified, and bacteria having a sequence similarity of 97% or more at the genus level were profiled using a BLASTN and GreenGenes 16S RNA sequence database (108,453 sequences) (QIIME).

As a result of performing metagenomic analysis on bacteria and bacteria-derived vesicles from stool of mice fed a regular CHO diet and a high fat diet for 12 weeks according to the above method, as illustrated in FIG. 2, it was confirmed that there was no difference in the distribution of bacteria belonging to the genus *Propionibacterium* between regular CHO diet-fed mice and high fat diet-fed mice, whereas the distribution of *Propionibacterium*-derived vesicles (EV) was significantly increased in stool of the high fat diet-fed mice, as compared to that of regular CHO diet-fed mice.

Example 2. Analysis of In Vivo Absorption, Distribution, and Excretion Patterns of Intestinal Bacteria and Bacteria-Derived Vesicles Experiments were conducted using the following method to evaluate whether intestinal bacteria and bacteria-derived vesicles were systemically absorbed through the gastrointestinal tract. Intestinal bacteria and intestinal bacteria-derived vesicles, which were labeled with fluorescence, were administered to the gastrointestinal tract of mice at a dose of 50 μg, and fluorescence was measured after 0 minute, 5 minutes, 3 hours, 6 hours, and 12 hours.

As a result of observing the whole images of mice, as illustrated in FIG. 3A, while the bacteria were not systemically absorbed, the bacteria-derived vesicles were systemically absorbed at 5 minutes after administration, strong fluorescence was observed in the bladder at 30 minutes after administration, thereby confirming that the vesicles were excreted into the urinary tract. In addition, it was confirmed that the vesicles were present in the body until 12 hours.

To evaluate the infiltration patterns of intestinal bacteria and intestinal bacteria-derived vesicles into various organs after being systemically absorbed, 50 μg of bacteria and bacteria-derived vesicles that were labeled with fluorescence were administered using the above-described method, and then blood, the heart, the liver, the kidneys, the spleen, fat, and muscle were collected 12 hours after administration.

As a result of observing fluorescence in the collected tissues, as illustrated in FIG. 3B, it was seen that the bacteria-derived vesicles were distributed in blood, the heart, the lungs, the liver, the kidneys, the spleen, fat, muscle, and the kidneys while the bacteria were not absorbed.

Example 3. Metagenomic Analysis of Bacteria-Derived Vesicles in Blood Samples from Normal People and Patients with Breast Cancer or Liver Cancer First, to isolate vesicles from blood samples of patients and normal people, blood was centrifuged (3,500×g, 10 minutes, 4° C.) to precipitate a floating material and only a supernatant was transferred into a new 10 ml tube. Bacteria and impurities were removed therefrom using a 0.22 μm filter, and then the resulting supernatant was transferred into Amicon Ultra Centrifugal Filters (50 kD), centrifuged at 1,500×g and 4° C. for 15 minutes to remove a material having a size of less than 50 kD, and concentrated up to 10 ml. Bacteria and impurities were removed again therefrom using a 0.22 μm filter, and then subjected to ultrahigh speed centrifugation at 150,000×g and 4° C. for 3 hours using a Type 90ti rotor to remove a supernatant, and the agglomerated pellet was dissolved with physiological saline (PBS).

Genes were extracted from vesicles present in blood samples of 96 patients with breast cancer and 191 normal people as a control having gender and age matched with those of the patients; and blood samples of 91 patients with liver cancer and 99 normal people as a control having gender and age matched with those of the patients, by using the above-described method.

As a result of evaluating the distribution of vesicles derived from bacteria belonging to the genus *Propionibacterium* at the genus level after metagenomic analysis was performed thereon using the method of Example 1, as illustrated in FIG. 5A, it was confirmed that vesicles derived from bacteria belonging to the genus *Propionibacterium* was significantly reduced in the blood samples of the patients with breast cancer, as compared to that in the blood samples of the normal people (normal people vs patients with breast cancer: 2.2% vs 0.5%; fold change: 0.23; p<0.000001).

In addition, as illustrated in FIG. 5B, it was confirmed that vesicles derived from bacteria belonging to the genus *Propionibacterium* was significantly reduced in the blood samples of the patients with liver cancer, as compared to that in the blood samples of the normal people (normal people vs patients with liver cancer: 1.7% vs 0.6%; fold change: 0.34, p=0.000001).

Example 4. Metagenomic Analysis of Bacteria-Derived Vesicles in Blood Samples of Normal People and Patients with Asthma or Atopic Dermatitis Genes were extracted from vesicles present in blood samples of 277 patients with asthma and 246 normal people as a control by using the method of Example 3. As a result of evaluating the distribution of vesicles derived from bacteria belonging to the genus *Propionibacterium* at the genus level after metagenomic analysis was performed thereon using the method of Example 1, as illustrated in FIG. 6A, it was confirmed that vesicles derived from bacteria belonging to the genus *Propionibacterium* was significantly reduced in the blood samples of the patients with asthma, as compared to that in the blood samples of the normal people (normal people vs patients with asthma: 1.8% vs 0.2%; fold change: 0.12, p<0.000001).

Genes were extracted from vesicles present in blood samples of 25 patients with atopic dermatitis and 138 normal people as a control by using the method of Example 3. As a result of evaluating the distribution of vesicles derived from bacteria belonging to the genus *Propionibacterium* at the genus level after metagenomic analysis was performed thereon using the method of Example 1, as illustrated in FIG. 6B, it was confirmed that vesicles derived from bacteria belonging to the genus *Propionibacterium* was significantly reduced in the blood samples of the patients with atopic dermatitis, as compared to that in the blood samples of the normal people (normal people vs patients with atopic dermatitis: 0.7% vs 0.1%; fold change: 0.15, p=0.000003).

Example 5. Metagenomic Analysis of
Bacteria-Derived Vesicles in Blood Samples of
Normal People and Patients with Diabetes or Liver
Cirrhosis Genes were extracted from vesicles present in blood samples of 73 patients with diabetes and 146 normal people as a control by using the method of Example 3. As a result of evaluating the distribution of vesicles derived from bacteria belonging to the genus *Propionibacterium* at the genus level after metagenomic analysis was performed thereon using the method of Example 1, as illustrated in FIG. 7A, it was confirmed that vesicles derived from bacteria belonging to the genus *Propionibacterium* was significantly reduced in the blood samples of the patients with asthma, as compared to that in the blood samples of the normal people (normal people vs patients with diabetes: 1.3% vs 0.01%; fold change: 0.01, p<0.000001).

Genes were extracted from vesicles present in blood samples of 100 patients with liver cirrhosis and 100 normal people as a control by using the method of Example 3. As a result of evaluating the distribution of vesicles derived from bacteria belonging to the genus *Propionibacterium* at the genus level after metagenomic analysis was performed thereon using the method of Example 1, as illustrated in FIG. 7B, it was confirmed that vesicles derived from bacteria belonging to the genus *Propionibacterium* was significantly reduced in the blood samples of the patients with liver cirrhosis, as compared to that in the blood samples of the normal people (normal people vs patients with liver cirrhosis: 1.4% vs 0.5%; fold change: 0.4, p=0.00004).

Example 6. Isolation of Vesicles from
*Propionibacterium acnes* Culture Solution and
Analysis of Characteristics Thereof Based on the results of Examples 3 to 5, a strain of *Propionibacterium acnes* was cultured and then vesicles were isolated therefrom, and characteristics of the vesicles were analyzed. The *P. acnes* 6919 strain was cultured in a brain heart infusion (BHI) medium in an anaerobic chamber at 37° C. until absorbance ($OD_{600}$) reached 1.0 to 1.5, and then sub-cultured. Subsequently, a *P. acnes* 6919 strain-free medium supernatant was collected and centrifuged at 10,000×g and 4° C. for 15 minutes, and the resulting supernatant was filtered using a 0.45 μm filter, and then concentrated to a volume of 200 ml through ultrafiltration using a 100 kDa hollow filter membrane by using a Quix-Stand benchtop system (GE Healthcare, UK). Thereafter, the concentrated supernatant was filtered again with a 0.22 μm filter, and the filtered supernatant was ultracentrifuged at 150,000×g and 4° C. for 3 hours, and then the pellet was suspended with DPBS. Next, density-gradient centrifugation was performed using 10%, 40%, and 50% OptiPrep solutions (Axis-Shield PoC AS, Norway), and the OptiPrep solutions were diluted with HEPES-buffered saline (20 mM HEPES, 150 mM NaCl, pH 7.4) to prepare a low-density solution. After centrifugation at 200,000×g and 4° C. for 2 hours, each solution fractionated at the same volume of 1 ml from the upper layer was further ultracentrifuged at 150,000×g and 4° C. for 3 hours. Thereafter, proteins were quantified using BCA assay, and the following experiments were performed on the obtained vesicles.

Vesicles were isolated from a culture solution of *Propionibacterium acnes* cultured according to the above method, and then the shape and size thereof were evaluated using an electron microscope.

As a result, as illustrated in FIG. 8A, it was observed that the vesicles isolated from the *Propionibacterium acnes* culture solution were spherical and had a size of less than 200 nm, and it was confirmed through dynamic light scattering measurement results shown in FIG. 8B that the vesicles had a size of 37.8±13.5 nm.

Example 7. Proteomic Analysis of
*Propionibacterium acnes*-Derived Vesicles

Proteomic analysis was performed to determine which proteins were included in *Propionibacterium acnes*-derived vesicles. For this, peptides digested with trypsin were obtained through a filter-aid sample preparation (FASP) digestion method. 18 μg of proteins extracted from the *Propionibacterium acnes*-derived vesicles were mixed with a reducing solution (4% SDS and 0.1 M DTT in 0.1 M Tris-HCl, pH 7.6), and then allowed to react at 37° C. for 45 minutes. The resulting solution was then boiled for 7 minutes, followed by filtration based on centrifugation at 14,000×g and 16° C. for 40 minutes. Additionally, the filtrate was mixed with a UA solution (0.2 mL of 8 M urea in 0.1 M Tris-HCl, pH 8.5) and repeatedly subjected to the centrifugation-based filtration three times, and then 0.1 ml of a 55 mM IAA solution was added thereto to allow a reaction to occur at room temperature in a dark room for 20 minutes, followed by centrifugation for 40 minutes. Similarly, samples were mixed with a UA solution and centrifugation-based filtration was repeatedly performed thereon three times, and then diluted with 0.2 ml of a 100 mM TEAB solution and centrifuged twice more to perform solution exchange for trypsin treatment. A filter was placed in a 1.5 ml tube, and a 100 mM TEAB solution containing high-purity trypsin was decomposed in the filter at 37° C. for 12 hours, followed by centrifugation at 14,000×g and 16° C. for 20 minutes, and then a process of adding 75 μl of the 100 mM TEAB solution thereto was repeated twice. The collected samples were dried with a SpeedVac concentrator, and then dissolved in 180 μl of a 5% ACN-dissolved solution (0.1% formic acid-dissolved distilled water as a solvent) and decontaminated with a C-18 rotary column (Thermo Scientific, USA), followed by vacuum-drying.

The dried samples were analyzed with a Q Exactive mass spectrometer (Thermo Fisher Scientific, Germany) connected to EASY nLC1000 (Thermo Fisher Scientific, Germany) using a nano-LC-ESI-MS/MS method. Peptides cleaved with trypsin were loaded onto a trapped column (75 μm×2 cm) packed with a C18 3-μm resin, and then eluted using a 5%-40% linear concentration gradient of a B solvent at a rate of 300 nl/min for 85 minutes. The eluted peptides were separated by an analytical column (75 μm×50 cm) packed with a C18 2-μm resin, and then electrosprayed to a nano ESI source at 2.0 kV. The Q Exactive mass spectrometer was operated using a top 10 data-dependent method. The most abundant precursor ions were selected by setting normalized collisional energy to 30% and setting dynamic exclusion time to 30 seconds and using a survey scan (m/z; 400-2,000) for higher-energy collisional dissociation separation. Survey MS scans were obtained with a resolution of 70,000 using an Orbitrap analyzer by setting HCD spectra resolution to 17,500.

Mass spectrometry (MS/MS) spectra obtained in three repetitions were searched for in the *Propionibacterium acnes* Uniprot database (2015. November reviewed) using the SEQUEST engine tool (Bioworks-Browser rev. 3.1 coupled with percolator validation). A maximum of two missed cleavage sites were included in the full tryptic specificity, and the mass tolerances of precursor ions and fragment ions were set at 10 ppm and 0.6 Da. The modification of carbamidomethyl cysteine was fixed, and various modifications of methionine oxidation were allowed. Peptides were screened with a cut-off value of FDR=0.01.

As a result, as illustrated in FIGS. 9A and 9B, among the proteins analyzed in the vesicles derived from *Propionibacterium acnes*, a total of 252 proteins were ultimately found by selecting highly reliable proteins detected twice or more in three repetitions. Proteome studies of *Propionibacterium acnes* have not been studied much, and thus the characteristics of more than a half of the analyzed proteins have not been well known. The distribution proportion of the analyzed proteins according to cellular components was analyzed as 27.4% for membrane-related proteins, 7.1% for cytoplasmic proteins, 1.2% for extracellular proteins, and 4.4% for liposome proteins. This means that the *Propionibacterium acnes*-derived vesicles are also enclosed in a membrane and include both cytoplasmic and extracellular proteins, like commonly known bacteria-derived vesicles. In addition, when the proteins were classified based on the distribution proportion according to biological function, the proteins were analyzed as 15.9% for metabolism, 7.5% for material transport, 5.2% for protein processing, 4.8% for translation, and 4% for pathogenicity. From the characteristics that proteins in the *Propionibacterium acnes*-derived vesicles are constituted at a very high rate in metabolism and material transport, it is anticipated that the *Propionibacterium acnes*-derived vesicles play a vital role in the metabolism and material transport of *Propionibacterium acnes*.

From the functions of the 252 proteins revealed by the proteomic analysis results, it can be seen that the *Propionibacterium acnes*-derived vesicles showed remarkable characteristics in terms of biochemical lifestyle, survival system, cell adhesion, pathogenicity, inflammation, and the like of *Propionibacterium acnes*.

Among the proteins in *Propionibacterium acnes*-derived vesicles, proteins associated with oxidative phosphorylation (cytochrome c oxidase, Rieske domain protein), nitrogen fixation (bacterial cytochrome ubiquinol oxidase, cytochrome d ubiquinol oxidase), anaerobic respiration (succinate dehydrogenases, methylmalonyl-CoA mutase), and substrate intake (ATP-binding cassettes) are present, and this is consistent with the fact that *Propionibacterium acnes* is non-aerobic and anaerobic and has a non-motile lifestyle. In addition, of the proteins in *Propionibacterium acnes*-derived vesicles, a considerable number thereof have functions related to transcription, translation, protein transport, and protein folding. From this, it may be anticipated that the *Propionibacterium acnes*-derived vesicles have a function such as intercellular transport of biochemical treatment- and energy metabolism-related substances or proteins, and function as a large transporter for transporting nutrients instead of non-motile *Propionibacterium acnes*.

In addition, from proteins that bind bacterial peptidoglycan layers or have resistance to penicillin, such as transglycosylase, beta-lactamase, multimodular transpeptidase-transglycosylase, FtsI, and the like, it may be anticipated that *Propionibacterium acnes* survives in an environment in which various types of bacteria are present, and uses vesicles derived from *Propionibacterium acnes* to exhibit antibiotic resistance in infectious regions.

From proteins that play a key role in adhering to cells or forming a biofilm, such as a putative uncharacterized protein (PPA2127) that binds to dermatan sulfate of a host to exhibit immunity, putative glycosyl-transferase that binds to epidermal cells of a host to form a biofilm, glyceraldehyde-3-phosphate dehydrogenase (GAPDH) that adheres to cells to exhibit pathogenicity by glycosylation, polysaccharide deacetylase that binds to epidermal cells and avoids immune responses of a damaged host from lysozyme, and the like, it may be anticipated that *Propionibacterium acnes* is capable of forming biological niches by using vesicles derived from *Propionibacterium acnes*.

From proteins, such as hyaluronate lyase that degrades the extracellular matrix of a host to induce an immune response in inflammatory cells, endoglycoceramidase that cleaves glycosphingolipid on cell surfaces and prevents signal transduction, endo-beta-N-acetylglucosaminidase H using a host cell-derived substrate as a metabolite, Christie-Atkins-Munch-Peterson (CAMP) factors that infiltrate into a host and disrupt cells by perforation to exhibit strong pathogenicity, and the like, it may be anticipated that vesicles derived from *Propionibacterium acnes* are efficiently delivered into cells.

It has been reported that an NlpC/P60 endopeptidase family protein, a basic membrane protein, 60 kDa chaperonin, 10 kDa chaperonin, and the like are essential proteins for the survival of *Propionibacterium acnes*, and exhibit immune responses against inflammatory cells via a defensive mechanism thereof when infiltrating into a host. From these facts, it can be seen that vesicles derived from *Propionibacterium acnes* can be used for immunomodulation by stimulating immune responses of a host using *Propionibacterium acnes*-derived proteins.

Proteins identified through proteomic analysis of the vesicles derived from *Propionibacterium acnes* are shown in Table 2 below.

TABLE 2

| Gene Name | Accession | Protein Name | GO-Biological Process | GO-Cellular Component |
|---|---|---|---|---|
| ftsY | W4U385_PROAA | Signal recognition particle receptor FtsY | SRP-dependent cotranslational protein targeting to membrane | Cytoplasm, Intrinsic component of plasma membrane |
| PAST3_05111 | A0A085B3F8_PROAA | Uncharacterized protein | — | integral component of membrane |
| JCM18909_1125 | W4TIQ5_PROAA | Uroporphyrinogen III decarboxylase | porphyrin-containing compound biosynthetic process | — |
| HMPREF9570_01608 | F1UIQ1_PROAA | Uncharacterized protein | — | integral component of membrane |
| HMPREF9344_01072 | A0A0E1YHC7_PROAA | Uncharacterized protein | — | — |
| JCM18918_946 | W4U3Y9_PROAA | L-proline glycine betaine ABC transport system permease protein ProW | — | — |
| pdxT | W4U4U3_PROAA | Pyridoxal 5'-phosphate synthase subunit PdxT | glutamine catabolic process, pyridoxal phosphate biosynthetic process, vitamin B6 biosynthetic process | — |
| JCM18920_273 | W4UDV8_PROAA | Uncharacterized protein | — | integral component of membrane |
| HMPREF9570_01578 | F1UIW0_PROAA | Uncharacterized protein | — | integral component of membrane |
| HMPREF9570_00330 | F1UEX6_PROAA | ABC transporter, solute-binding protein | — | — |
| HMPREF9206_0523 | D1YFC9_PROAA | Uncharacterized protein | — | integral component of membrane |
| JCM18918_3895 | W4U9Z7_PROAA | Dolichol-phosphate mannosyltransferase | — | — |
| JCM18916_1395 | W4TTY6_PROAA | Glutamine synthetase type I | Nitrogen compound metabolic process | — |
| JCM18918_383 | W4U0P5_PROAA | Dolichol-phosphate mannosyltransferase | — | — |
| JCM18909_3341 | W4TNE4_PROAA | Uncharacterized protein | — | integral component of membrane |
| HMPREF9344_00075 | A0A0E1YK98_PROAA | Succinate CoA transferase | acetyl-CoA metabolic process | — |
| PAST3_07564 | A0A085B206_PROAA | Fructose-bisphosphate aldolase | glycolytic process | — |
| HMPREF9570_01325 | F1UI30_PROAA | Uncharacterized protein | — | integral component of membrane |
| HMPREF9344_01711 | A0A0E1YH92_PROAA | ErfK/YbiS/YcfS/YnhG | — | — |
| HMPREF1162_1003 | F9NXK4_PROAA | Pyridine nucleotide-disulfide oxidoreductase | — | — |
| HMPREF9578_01543 | E6D3Y4_PROAA | ErfK/YbiS/YcfS/YnhG | — | — |
| HMPREF9344_01854 | A0A0E1YI81_PROAA | Uncharacterized protein | — | integral component of membrane |
| JCM18918_3903 | W4UAZ1_PROAA | 2,3,4,5-tetrahydropyridine-2,6-dicarboxylate N-acetyltransferase | — | — |
| JCM18920_1123 | W4UEG5_PROAA | 2,4-dienoyl-CoA reductase | — | — |
| JCM18916_1756 | W4TVT1_PROAA | Uncharacterized protein | photosynthesis, light reaction | plasma membrane light-harvesting complex |

TABLE 2-continued

| Gene Name | Accession | Protein Name | GO-Biological Process | GO-Cellular Component |
|---|---|---|---|---|
| JCM18909_4054 | W4TQJ4_PROAA | Uncharacterized protein | — | integral component of membrane |
| PAST3_01596 | A0A085B4Q8_PROAA | Putative glycosyl transferase | — | — |
| JCM18916_2713 | W4TXW7_PROAA | Uncharacterized protein | — | integral component of membrane |
| HMPREF9344_01464 | A0A0E1YGY4_PROAA | Aminotransferase, class I/II | — | — |
| rpoB | R4L3U6_PROAA | DNA-directed RNA polymerase (Fragment) | transcription, DNA-templated | — |
| sdhA | D4HEX0_PROAS | Succinate dehydrogenase flavoprotein subunit | — | — |
| JCM18918_3293 | W4UA75_PROAA | Uncharacterized protein | — | integral component of membrane |
| JCM18920_3008 | W4UKV6_PROAA | DNA-directed RNA polymerase | Transcription, DNA-templated | — |
| rpsJ | F1UKL8_PROAA | 30S ribosomal protein S10 | translation | ribosome |
| HMPREF1162_2086 | F9NXA8_PROAA | Peptidase C1-like protein | — | — |
| JCM18916_3283 | W4TYC7_PROAA | Uncharacterized protein | — | integral component of membrane |
| JCM18916_839 | W4TSZ0_PROAA | Elongation factor Ts | — | small ribosomal subunit |
| coxB | D4HCM6_PROAS | Cytochrome c oxidase, subunit II | electron transport chain | integral component of membrane |
| JCM18916_1312 | W4TUQ7_PROAA | Uncharacterized protein | — | integral component of membrane |
| rplL | RL7_PROAC | 50S ribosomal protein L7/L12 | translation | ribosome |
| cbiN | A0A085B001_PROAA | Cobalt transport protein CbiN | cobalamin biosynthetic process | integral component of membrane, plasma membrane |
| JCM18920_2186 | W4UIY5_PROAA | Outer membrane protein A | — | Cell outer membrane, Integral component of membrane |
| rplQ | F1UKD4_PROAA | 50S ribosomal protein L17 | translation | ribosome |
| rplS | W4UI67_PROAA | 50S ribosomal protein L19 | translation | ribosome |
| JCM18909_475 | W4TF81_PROAA | Methylmalonyl-CoA mutase | — | — |
| JCM18909_2328 | W4TLS3_PROAA | LSU ribosomal protein L5p | ribosome | translation |
| JCM18916_3017 | W4TXR1_PROAA | CAMP factor | — | — |
| JCM18909_473 | W4TH18_PROAA | Methylmalonyl-CoA mutase | — | — |
| PPA2127 | E2ICJ6_PROAA | Putative uncharacterized protein (Fragment) | — | — |
| JCM18918_1025 | W4U2V0_PROAA | Signal peptidase I | protein processing involved in protein targeting to mitochondrion | integral component of membrane |
| JCM18920_1269 | W4UFS4_PROAA | Methylmalonyl-CoA:pyruvate transcarboxylase | — | — |
| HMPREF0675_5348 | D4HBJ7_PROAS | SH3 domain protein | — | — |
| N/A | Q50E66_PROAA | CAMP factor 2 | — | — |
| HMPREF1162_1035 | F9NXN7_PROAA | Tricorn protease homolog | — | cytoplasm |
| HMPREF9344_00824 | A0A0E1YKT1_PROAA | Hyaluronate lyase | Carbohydrate metabolic process | Extracellular region |

TABLE 2-continued

| Gene Name | Accession | Protein Name | GO-Biological Process | GO-Cellular Component |
|---|---|---|---|---|
| N/A | Q5QCW8_PROAA | Camp2 | — | — |
| HMPREF9344_01393 | A0A0E1YGP6_PROAA | NlpC/P60 family protein | — | — |
| HMPREF9344_01070 | A0A0E1YTB5_PROAA | Tricorn protease homolog | — | cytoplasm |
| PAST3_10318 | A0A085B0H7_PROAA | Beta-N-acetylhexosaminidase | Carbohydrate metabolic process | — |
| JCM18920_1344 | W4UFZ3_PROAA | CAMP factor | — | — |
| JCM18918_2370 | W4U6W5_PROAA | Peptidase E | — | — |
| hflB | A0A0E1YKG2_PROAA | ATP-dependent zinc metalloprotease FtsH | protein catabolic process | integral component of membrane, plasma membrane |
| HMPREF9344_00204 | A0A0E1YLS2_PROAA | SH3 domain protein | — | — |
| PAST3_08146 | A0A085B1J8_PROAA | Serine acetyltransferase | cysteine biosynthetic process from serine | cytoplasm |
| HMPREF1162_1127 | F9NUI0_PROAA | Bacterial SH3 domain protein | — | — |
| HMPREF9578_02632 | E6DAK7_PROAA | Periplasmic binding protein | — | — |
| rpsE | A0A085B5C6_PROAA | 30S ribosomal protein S5 | Translation | Small ribosomal subunit |
| HMPREF9344_00841 | A0A0E1YLV6_PROAA | ABC transporter, ATP-binding protein | — | — |
| HMPREF9570_02049 | F1UK58_PROAA | ABC transporter, solute-binding protein | — | — |
| JCM18909_3059 | W4TNL8_PROAA | ABC transporter ATP-binding protein | — | — |
| rpsD | F1UKD2_PROAA | 30S ribosomal protein S4 | translation | small ribosomal subunit |
| JCM18916_3143 | W4TY03_PROAA | ABC transporter ATP-binding protein | — | — |
| HMPREF9578_00861 | E6D6Z0_PROAA | Sugar-binding domain protein | — | — |
| rpsF | A0A085B274_PROAA | 30S ribosomal protein S6 | translation | ribosome |
| JCM18920_3587 | W4ULS0_PROAA | ABC transporter | — | — |
| PA4687 | Q06WK8_PROAA | HtaA-like surface protein | — | — |
| atpA | A0A085B090_PROAA | ATP synthase subunit alpha | ATP hydrolysis coupled proton transport, plasma membrane ATP synthesis coupled proton transport | — |
| rplN | F9NX47_PROAA | 50S ribosomal protein L14 | translation | large ribosomal subunit |
| HMPREF9570_00519 | F1UFZ3_PROAA | Periplasmic binding protein | — | — |
| HMPREF0675_4199 | D4HDU5_PROAS | Beta-lactamase | — | — |
| JCM18916_557 | W4TRS6_PROAA | ATP synthase gamma chain | ATP synthesis coupled proton transport | — |
| JCM18916_980 | W4TSU8_PROAA | Membrane protein | — | — |
| HMPREF0675_4855 | D4H9R7_PROAS | Triacylglycerol lipase | — | — |
| JCM18918_412 | W4U2L4_PROAA | ATP synthase beta chain | ATP synthesis coupled proton transport | — |
| JCM18920_1413 | W4UG55_PROAA | ATP synthase delta chain | ATP synthesis coupled proton transport | membrane |
| JCM18909_3148 | W4TN95_PROAA | Enoyl-[acyl-carrier-protein] reductase | — | — |

TABLE 2-continued

| Gene Name | Accession | Protein Name | GO-Biological Process | GO-Cellular Component |
|---|---|---|---|---|
| tmRNAPropi_acnes_SK137 | V6BXX0_PROAA | Proteolysis tag peptide encoded by tmRNA Propi_acnes_SK137 (Fragment) | — | — |
| HMPREF9570_01661 | F1UJ13_PROAA | Kinase domain protein | — | — |
| JCM18916_1386 | W4TUE1_PROAA | PTS system | phosphoenolpyruvate-dependent sugar phosphotransferase system | integral component of membrane, plasma membrane |
| HMPREF9570_00339 | F1UEY5_PROAA | Uncharacterized protein | — | — |
| pgk | A0A085B4M9_PROAA | Phosphoglycerate kinase | glycolytic process | cytoplasm |
| JCM18918_1238 | W4U4T1_PROAA | MoxR-like ATPases | — | — |
| JCM18918_4037 | W4UAB5_PROAA | PTS system | phosphoenolpyruvate-dependent sugar phosphotransferase system | — |
| JCM18918_3273 | W4U8C3_PROAA | Inosine-5'-monophosphate dehydrogenase | — | — |
| purL | W4THC8_PROAA | Phosphoribosylformylglycinamidine synthase subunit PurL | de novo' IMP biosynthetic process | cytoplasm |
| JCM18918_1333 | W4U3P8_PROAA | Cytochrome c oxidase polypeptide I | — | — |
| JCM18918_303 | W4U2A8_PROAA | Protein YceG like | — | — |
| sucC | A0A085B1K8_PROAA | Succinyl-CoA ligase [ADP-forming] subunit beta | tricarboxylic acid cycle | — |
| tatA | A0A085B0L5_PROAA | Sec-independent protein translocase protein TatA | Protein secretion, Protein transport by the Tat complex | Integral component of plasma membrane, TAT protein transport complex |
| PAST3_07599 | A0A085B213_PROAA | Biotin carboxyl carrier protein of methylmalonyl-CoA:Pyruvate transcarboxylase | — | — |
| JCM18916_723 | W4TR26_PROAA | Lysine-tRNA ligase | lysyl-tRNA aminoacylation | cytoplasm |
| rho | W4U2H4_PROAA | Transcription termination factor Rho | DNA-templated transcription, termination, regulation of transcription, DNA-templated | — |
| JCM18909_1988 | W4TKY5_PROAA | Cation diffusion facilitator family transporter | — | — |
| HMPREF9570_01974 | F1UJY3_PROAA | Uncharacterized protein | — | integral component of membrane |
| PAST3_09633 | A0A085B110_PROAA | ABC-type transporter, periplasmic component | — | — |
| JCM18916_3759 | W4TZ18_PROAA | Preprotein translocase subunit SecE | Protein secretion, Protein targeting | Integral component of membrane, Intracellular |
| glyQS | A0A085B438_PROAA | Glycine-tRNA ligase | glycyl-tRNA aminoacylation | cytoplasm |
| HMPREF9206_1837 | D1YCA6_PROAA | Tat pathway signal sequence domain protein | — | — |
| HMPREF9344_02504 | A0A0E1YDI6_PROAA | Lon protease (S16) C-terminal proteolytic domain protein | protein catabolic process | integral component of membrane |

TABLE 2-continued

| Gene Name | Accession | Protein Name | GO-Biological Process | GO-Cellular Component |
|---|---|---|---|---|
| secD | D4HDW9_PROAS | Protein translocase subunit SecD | Intracellular protein transmembrane transport, Proteintargeting, ProteintransportbytheSeccomplex | Integral component of membrane, Intracellular, Plasma membrane |
| JCM18916_470 | W4TSE3_PROAA | Enzyme of poly-gamma-glutamate biosynthesis | — | — |
| groL | A0A085B1J1_PROAA | 60 kDa chaperonin | Protein refolding | cytoplasm |
| HMPREF9570_00463 | F1UFN7_PROAA | ABC transporter, solute-binding protein | — | — |
| groL | E6D9F5_PROAA | 60 kDa chaperonin | Protein refolding | cytoplasm |
| groS | CH10_PROAC | 10 kDa chaperonin | protein folding | cytoplasm |
| JCM18920_241 | W4UCN3_PROAA | PspA/IM30 family protein | — | — |
| secA | A0A0E1YDL8_PROAA | Protein translocase subunit SecA | intracellular protein transmembrane transport, protein import, protein targeting | cytoplasm, plasma membrane |
| pstS | F1UIJ3_PROAA | Phosphate-binding protein PstS | phosphate ion transmembrane transport | — |
| JCM18916_1981 | W4TVZ8_PROAA | Heme ABC transporter | — | — |
| HMPREF9578_01591 | E6D431_PROAA | FHA domain protein | — | — |
| HMPREF9344_02598 | A0A0E1YF67_PROAA | Peptidyl-prolyl cis-trans isomerase | Protein folding | — |
| JCM18918_4160 | W4UBK0_PROAA | Cell envelope-related function transcriptional attenuator | — | — |
| JCM18920_274 | W4UC57_PROAA | Peptidyl-prolyl cis-trans isomerase | protein folding | — |
| JCM18916_1704 | W4TTJ3_PROAA | ABC transporter ATP-binding protein | — | — |
| JCM18909_251 | W4TFA1_PROAA | Peptidyl-prolyl cis-trans isomerase | protein folding | — |
| JCM18909_2781 | W4TM00_PROAA | Argininosuccinate synthase | Arginine biosynthetic process | cytoplasm |
| JCM18918_2061 | W4U6R2_PROAA | Integral membrane protein | — | integral component of membrane |
| JCM18909_1400 | W4THK0_PROAA | NADH-ubiquinone oxidoreductase | — | — |
| JCM18918_1420 | W4U3H8_PROAA | Arginine deiminase | arginine catabolic process | — |
| HMPREF9570_00243 | F1UES3_PROAA | Uncharacterized protein | — | — |
| JCM18916_2258 | W4TX28_PROAA | Cell division protein FtsI | Cell division | — |
| pepA | AMPA_PROAC | Probable cytosol aminopeptidase | — | cytoplasm |
| JCM18916_3790 | W4TZQ4_PROAA | Uncharacterized protein | — | — |
| JCM18916_1932 | W4TU75_PROAA | Cell division protein FtsI | Cell division | — |
| metN | D4H9G7_PROAS | Methionine import ATP-binding protein MetN | — | — |
| JCM18916_3473 | W4TZX4_PROAA | Uncharacterized protein | — | — |

Example 8. Anti-Inflammatory Effect of *Propionibacterium acnes*-Derived Vesicles To examine an effect of *Propionibacterium acnes*-derived vesicles on the secretion of inflammatory mediators in inflammatory cells, Raw 264.7 cells, which is a mouse macrophage line, were treated with *Propionibacterium acnes*-derived vesicles (*P. acnes* EV) at various concentrations (0.001, 0.01, 0.1, 1, or 10 ng/ml), and then the secretion amounts of inflammatory mediators (IL-6, TNF-α, and the like) were measured through apoptosis and ELISA (R&D System, USA). More specifically, Raw 264.7 cells were dispensed into a 24-well cell culture plate at a density of $1 \times 10^5$ cells/well, and then cultured in a DMEM complete medium for 24 hours. Subsequently, apoptosis was assessed by MTT assay (Sigman, USA). In addition, to evaluate the ability thereof to secrete inflammatory mediators, the medium was removed and the *Propionibacterium acnes*-derived vesicles were mixed and treated with a new DMEM complete medium, and then incubated in an incubator at 37° C. from 6 hours to 24 hours to obtain a culture supernatant. The culture supernatant was collected in a 1.5 ml tube and centrifuged at 3,000×g for 5 minutes, and the supernatant was collected and stored at 4° C., followed by ELISA analysis.

For ELISA analysis, the capture antibody was diluted with PBS and the diluted solution was dispensed in 50 µl aliquots into a 96-well polystyrene plate in accordance with an operating concentration, and then allowed to react at 4° C. overnight. Subsequently, the sample was washed twice with 100 µl of a PBST (0.05% TWEEN® 20-containing PBS) solution, and then an RD (1% BSA-containing PBST) solution was dispensed in 100 µl aliquots into the plate, followed by blocking at room temperature for 1 hour and washing twice again with 100 µl of PBST, and then the sample and a standard were dispensed in 50 µl aliquots in accordance with concentration and allowed to react at room temperature for 2 hours. The sample and the standard were washed twice again with 100 µl of PBST, and then the detection antibody was diluted with RD, and the diluted solution was dispensed into 50 µl aliquots in accordance with an operating concentration and allowed to react at room temperature for 2 hours. The sample and the standard were washed twice again with 100 µl of PBST, and then Strpetavidin-HRP was diluted in RD to 1/200, and the diluted solution was dispensed in 50 µl aliquots and allowed to react at room temperature for 30 minutes. Lastly, the sample and the standard were washed three times with 100 µl of PBST, and then a solution prepared by mixing a TMB substrate and 0.04% oxygenated water in a ratio of 1:1 was dispensed in 50 µl aliquots. Thereafter, color developing was waited for and when color was developed after 5 minutes to 20 minutes, a 1M sulfuric acid solution was dispensed in 50 µl aliquots, the reaction was stopped, and absorbance at 450 nm was measured using a Synergy™ HT multi-detection microplate reader (BioTek, USA).

As a result, as illustrated in FIG. 10A, the apoptosis of inflammatory cells was not induced regardless of the treatment concentration of *Propionibacterium acnes*-derived vesicles.

In addition, as illustrated in FIG. 10B, it was confirmed that the secretion of macrophage inflammatory mediators by treatment with the *Propionibacterium acnes*-derived vesicles was significantly reduced, as compared to that of *E. coli* vesicles (*E. coli* EV), which are pathogenic vesicles.

From these results, it was confirmed that *Propionibacterium acnes*-derived vesicles were much safer when absorbed into the body.

To evaluate an anti-inflammatory effect of *Propionibacterium acnes*-derived vesicles, based on the above-described results, various concentrations of *Propionibacterium acnes*-derived vesicles were administered to a macrophage line 12 hours before being treated with *E. coli*-derived vesicles (at a concentration of 1 µg/ml), and then the secretion of inflammatory cytokines due to the *E. coli*-derived vesicles was measured by ELISA.

As a result, as illustrated in FIGS. 11A and 11B, it was confirmed that, in the case of pretreatment with the *Propionibacterium acnes*-derived vesicles, the secretion of IL-6 and TNF-α due to the *E. coli*-derived vesicles was significantly inhibited. This means that *Propionibacterium acnes*-derived vesicles are able to efficiently inhibit inflammatory diseases such as asthma and the like and metabolic diseases such as diabetes and the like, which are induced by pathogenic vesicles such as *E. coli*-derived vesicles.

Example 9. Anti-Apoptotic Effect of *Propionibacterium acnes*-Derived Vesicles on Apoptosis of Skin Keratinocytes Due to *Staphylococcus aureus*-Derived Vesicles To evaluate an inhibitory effect of *Propionibacterium acnes*-derived vesicles on the apoptosis of skin epithelial cell due to *Staphylococcus aureus*-derived vesicles, the same pretreatment process as that used in Example 8 was performed using a keratinocyte line (HaCaT cells) instead of the macrophage line, and then the pretreated keratinocyte line was treated with *Staphylococcus aureus*-derived vesicles or *Propionibacterium acnes*-derived vesicles for 24 hours, followed by MTT assay (Sigman, USA).

As a result, as illustrated in FIGS. 12A and 12B, it was confirmed that the *Propionibacterium acnes*-derived vesicles significantly reduced the apoptosis of keratinocytes, as compared to the *Staphylococcus aureus*-derived vesicles.

To evaluate an inhibitory effect of *Propionibacterium acnes*-derived vesicles on the apoptosis of skin keratinocytes due to *Staphylococcus aureus*-derived vesicles, based on the above-described results, various concentrations of *Propionibacterium acnes*-derived vesicles were administered to a keratinocyte line 12 hours before being treated with *Staphylococcus aureus*-derived vesicles (at a concentration of 100 µg/ml), followed by MTT assay (Sigman, USA).

As a result, as illustrated in FIG. 13, it was confirmed that, in the case of pretreatment with the *Propionibacterium acnes*-derived vesicles, the apoptosis of keratinocytes due to the *Staphylococcus aureus*-derived vesicles was inhibited. This means that *Propionibacterium acnes*-derived vesicles are able to efficiently inhibit skin diseases induced by pathogenic vesicles such as *Staphylococcus aureus*-derived vesicles.

Example 10. Effect of *Propionibacterium acnes*-Derived Vesicles on Expression of Androgen Receptors It was confirmed through Examples 3 and 5 that vesicles derived from bacteria belonging to the genus *Propionibacterium* was significantly reduced in blood samples of patients with breast cancer or atopic dermatitis, as compared to that of normal people, and thus a therapeutic mechanism of the vesicles for atopic dermatitis, breast cancer, and the like was specifically examined. For this, as depicted in FIG. 14, 6-week-old male C57BL/6 mice were treated with *Propionibacterium acnes*-derived vesicles to evaluate the expression of androgen receptors in mouse prostate tissues. 1 µg of *Propionibacterium acnes*-derived vesicles (PaEV) was intraperitoneally injected into experimental groups each including three mice twice a week for a total of 4 weeks, and PBS or 1 µg of peptidoglycan (PGN) and 1 µg of lipoteichoic acid (LTA), which are well-known antigens of *Propionibacterium acnes*-derived vesicles, was intraperitoneally injected into a control twice a week for a total of 4 weeks. 3 days after the last injection, the prostate tissue was extracted and ground to obtain a supernatant, and the expression pattern of an androgen receptor (AR) was examined by western blotting.

For western blotting analysis, the extracted mouse prostate tissue was transferred to a 1.5 ml tube, and then quickly cooled in liquid nitrogen. Subsequently, a lysis solution was added thereto, and beads were added to grind the tissue with Tissuelyser II (Qiagen, Germany). The ground tissue solution was transferred to a new 1.5 ml tube and centrifuged at 17,000×g and 4° C. for 15 minutes to obtain a supernatant, and this process was repeated twice. Proteins of the supernatant were quantified using a BCA analysis method. 150 μg of the protein sample was mixed with a loading solution and subjected to SDS-PAGE at 160 V for 1 hour in a 4% stacking gel and 7.5% separating gel, and then the PA gel was transferred to a PVDF membrane activated in 100% ethanol for 5 minutes in an ice bucket at 400 mA for 50 minutes. The transferred PVDF membrane was shaking-incubated in an RD solution (TBS-T containing 5% skim milk) at room temperature for 40 minutes. Subsequently, the resulting PVDF membrane was washed three times with TBS-T for 30 minutes, and then primary antibodies for an androgen receptor were diluted with RD to 1/4000, followed by shaking incubation at room temperature for 1.5 hours. The resulting PVDF membrane was washed three times with TBS-T for 30 minutes, and then secondary antibodies were diluted with RD to 1/4000, followed by shaking incubation at room temperature for 1 hour. The resulting PVDF membrane was washed three times with TBS-T for 30 minutes, and then an ECL femto substrate (Thermo Scientific, USA) was diluted with distilled water to 1/10 to be sprayed onto the PVDF membrane, and a western image was acquired using a LAS-4000 device (GE Healthcare, UK). A western image for β-actin was used as a control.

As a result, as illustrated in FIG. 14, it was confirmed that, unlike peptidoglycan (PGN) and lipoteichoic acid (LTA), which are well-known antigens, when *Propionibacterium acnes*-derived vesicles were administered, an androgen receptor was overexpressed in the prostate tissue. It can be seen from phenomena in which an androgen receptor is stimulated for the treatment of breast cancer and atopic dermatitis is alleviated during puberty when the expression of an androgen receptor is increased that *Propionibacterium acnes*-derived vesicles exhibit therapeutic efficacy by increasing the expression of an androgen receptor, which is one of the therapeutic mechanisms. In addition, it may be anticipated that the overexpression of an androgen receptor is caused by protein components other than non-protein components such as PGN and LTA in *Propionibacterium acnes*-derived vesicles.

The foregoing description of the present invention is provided for illustrative purposes only, and it will be understood by those of ordinary skill in the art to which the present invention pertains that the present invention may be easily modified in other particular forms without changing the technical spirit or essential characteristics of the present invention. Thus, the above-described embodiments should be construed as being provided for illustrative purposes only and not for purposes of limitation.

INDUSTRIAL APPLICABILITY

Vesicles derived from bacteria belonging to the genus *Propionibacterium*, according to the present invention, increase the expression of an androgen receptor in prostate tissue, and have an anti-inflammatory effect and an immunoregulatory effect when inflammatory cells are pretreated therewith, and thus it is anticipated that the vesicles can be usefully used in methods of diagnosing or predicting cancer, an inflammatory disease, an endocrine disease, or a metabolic disease, pharmaceutical compositions, foods, cosmetics, and the like.

The invention claimed is:

1. A method of preventing or treating cancer or an inflammatory disease, the method comprising administering, to an individual, a pharmaceutical composition comprising, as an active ingredient, vesicles derived from *Propionibacterium acnes*, wherein the cancer is breast cancer, and wherein the inflammatory disease is atopic dermatitis or asthma.

2. The method of claim 1, wherein the vesicles have an average diameter of 10 nm to 1,000 nm.

3. The method of claim 1, wherein the vesicles are naturally or artificially secreted from the *Propionibacterium acnes*.

4. The method of claim 1, wherein the composition is an inhalant.

* * * * *